US009354231B1

(12) United States Patent
Glover

(10) Patent No.: US 9,354,231 B1
(45) Date of Patent: May 31, 2016

(54) REACTIVE SELF-INDICATING ABSORBENT MATERIALS, METHODS, AND SYSTEMS

(75) Inventor: Thomas Grant Glover, Bel Air, MD (US)

(73) Assignee: Leidos, Inc., Reston, VA (US)

(*) Notice: Subject to any disclaimer, the term of this patent is extended or adjusted under 35 U.S.C. 154(b) by 1165 days.

(21) Appl. No.: 13/189,736

(22) Filed: Jul. 25, 2011

(51) Int. Cl.
*G01N 27/403* (2006.01)
*G01N 33/543* (2006.01)

(52) U.S. Cl.
CPC .......... *G01N 33/5438* (2013.01); *G01N 27/403* (2013.01)

(58) Field of Classification Search
CPC . G01N 33/5438; G01N 27/403; G01N 27/06; G01N 30/96; G01N 27/021; G01N 27/3271; G01N 2030/965; G01N 27/126; G01N 27/12; G01N 27/60; G01N 33/0031; G01N 27/002; B01J 19/0046; B01J 2219/00527; B01J 2219/00585
USPC .......................................... 436/149, 150, 151
See application file for complete search history.

(56) References Cited

U.S. PATENT DOCUMENTS 4,254,616 A * 3/1981 Siminski et al. ............. 60/39.12
6,202,471 B1 * 3/2001 Yadav et al. .................. 73/31.05

OTHER PUBLICATIONS

Adsorption of Sulfur Dioxide by CoFe2O4 Spinel Ferrite Nanoparticles and Corresponding Changes in Magnetism T. Grant Glover, Daniel Sabo, Lisa A. Vaughn, Joseph A. Rossin, and Z. John Zhang Langmuir 2012, 28, 5695-5702.*

Chemisorption of Cyanogen Chloride by Spinel Ferrite Magnetic Nanoparticles T. Grant Glover, Jared B. DeCoste, Daniel Sabo, and Z. John Zhang Langmuir 2013, 29, 5500-5507.*
Glover, T. Grant, et al., "Carbon-Silica Composite Adsorbent: Characterization and Adsorption of Light Gases," *Microporous and Mesoporous Materials*, 111, pp. 1-11, 2008.
Peterson, Gregory W., et al., "Ammonia Vapor Removal by $Cu_3(BTC)_2$ and Its Characterization by MAS NMR," *Journal of Physical Chemistry C*, 113, pp. 13906-13917, 2009.
Britt, David, et al., "Highly Efficient Separation of Carbon Dioxide by a Metal-Organic Framework Replete With Open Metal Sites," *Proceedings of the National Academy of Science*, vol. 106, No. 49, pp. 20637-20640, Dec. 8, 2009.
Britt, David, et al., "Metal-Organic Frameworks With High Capacity and Selectivity for Harmful Gases," *Proceedings of the National Academy of Science*, vol. 105, No. 33, pp. 11623-11627, Aug. 19, 2008.

* cited by examiner

*Primary Examiner* — Krishnan S Menon
*Assistant Examiner* — Dwan A Gerido
(74) *Attorney, Agent, or Firm* — Dawn-Marie Bey; Bey & Cotropia PLLC

(57) ABSTRACT

The present disclosure relates, according to some embodiments, reactive self-indicating adsorbent materials, methods, and systems. A system may comprise, for example, a reactive self indicating adsorbent material, wherein the reactive self indicating adsorbent material comprises at least one super paramagnetic particle and a semi permeable support, wherein the at least one super paramagnetic particle is configured such that at least one magnetic property of the at least one super paramagnetic particle changes upon contact with an adsorbate; and/or at least one detector configured and arranged to detect the at least one magnetic property. In some embodiments, a method for assessing the performance and/or remaining life of an adsorbent material may comprise (a) contacting a fluid comprising an adsorbate with the adsorbent material under conditions that permit the adsorbate to contact the at least one super paramagnetic particle, wherein a change in a magnetic property of the at least one super paramagnetic particle occurs upon contact with the adsorbate; (b) detecting the magnetic property of the at least one super paramagnetic particle; and/or (c) comparing the detected magnetic property to a reference to produce an assessment of the performance and/or remaining life of the adsorbent material.

16 Claims, 22 Drawing Sheets

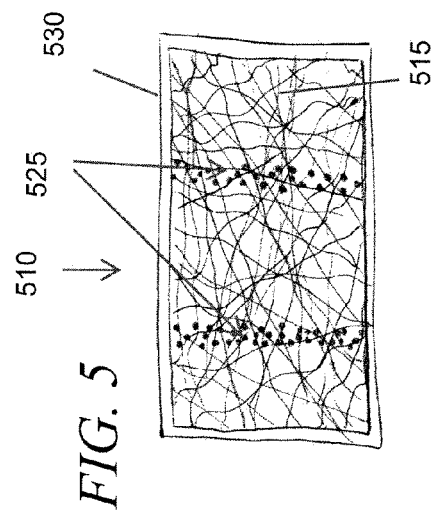
FIG. 5
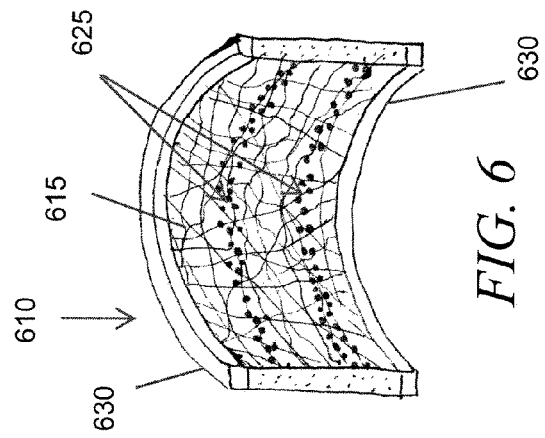
FIG. 6
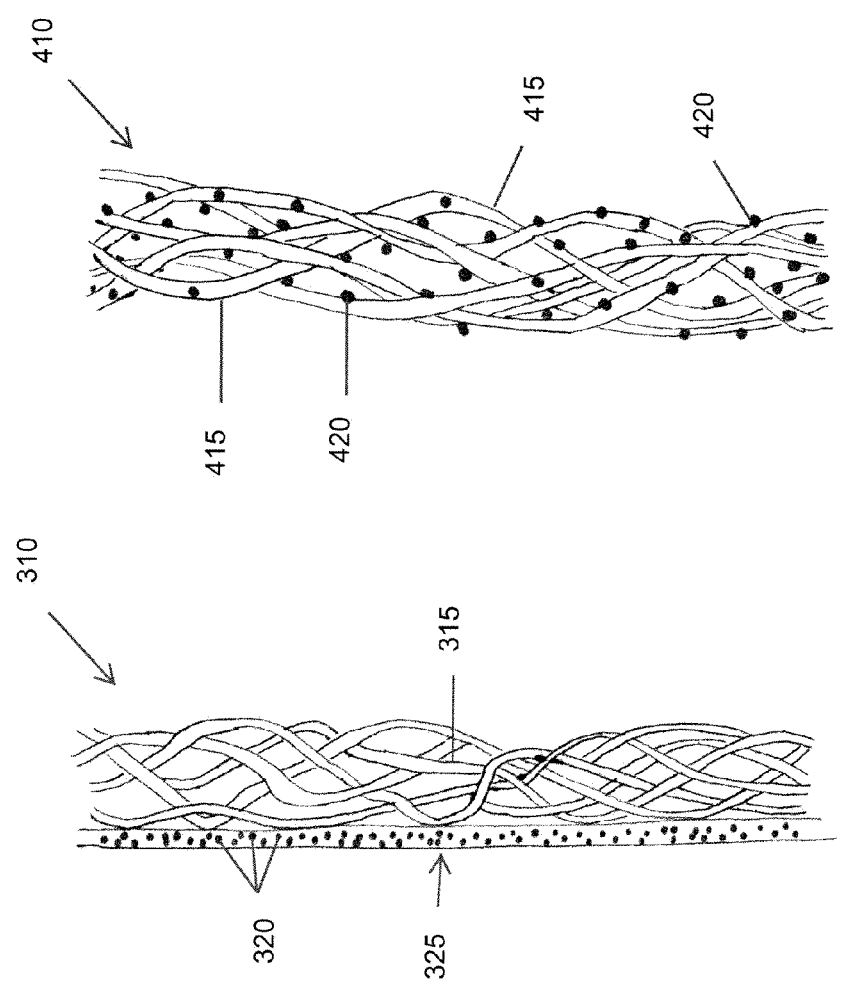
FIG. 4
FIG. 3

REACTIVE SELF-INDICATING ABSORBENT MATERIALS, METHODS, AND SYSTEMS

FIELD OF THE DISCLOSURE

The present disclosure relates, in some embodiments, reactive self-indicating adsorbent materials, methods, and systems.

BACKGROUND OF THE DISCLOSURE

Frequently filters are simply changed on a set schedule regardless of their ongoing performance and/or remaining capacity. For example, the filters that are used in research buildings to filter hood exhausts are typically changed on a schedule regardless of remaining filter capacity. This approach may be inefficient in that filters may be changed prior to exhaustion and/or ineffective in that filters may be left in use beyond their actual ability to perform.

Determining the remaining life of a carbon air filter may be encumbered by a need to remove it from service. For example, upon removal of a filter from service, a carbon sample may be taken from the filter and properties of the carbon may be assessed in a lab. Or the selected filter itself may be challenged with a probe chemical until the filter life is reached. For example, a pulse of adsorbing gas may be introduced into the system and the time necessary for the pulse to exit the filter assessed. In either case, the filter must be removed from the filter housing and probed. A war-fighter, for example, may lack a quick, on-site, means of assessing the level of protection remaining in his collective protection system. Assessing filter performance may be costly (e.g., for filter down time, analytic reagents, and/or dedicated lab facilities needed) and may still fall short of delivering real time assessments of performance and/or remaining filter life.

SUMMARY

Accordingly, a need has arisen for improved means for assessing one or more aspects of a filter (e.g., performance and/or remaining filter life) while reducing down time and/or costs.

The present disclosure relates, in some embodiments, reactive self-indicating adsorbent materials, methods, and systems. For example, the present disclosure provides methods for assessing the performance and/or remaining life of an adsorbent material comprising at least one super paramagnetic particle. In some embodiments, a method for assessing the performance and/or remaining life of an adsorbent material may comprise (a) contacting (e.g., continuously contacting, intermittently contacting, periodically contacting, sporadically contacting, haphazardly contacting, or combinations thereof.) a fluid comprising an adsorbate with the adsorbent material under conditions that permit the adsorbate to contact the at least one super paramagnetic particle, wherein a change in a magnetic property of the at least one super paramagnetic particle occurs upon contact with the adsorbate; (b) detecting (e.g., continuously detecting, intermittently detecting, periodically detecting, sporadically detecting, haphazardly detecting, or combinations thereof.) the magnetic property of the at least one super paramagnetic particle; and/or (c) comparing the detected magnetic property to a reference to produce an assessment of the performance and/or remaining life of the adsorbent material. Detecting a magnetic property may be concurrent (e.g., coextensive) with contacting a fluid with an adsorbent material according to some embodiments. Detecting a magnetic property, in some embodiments, may be non-invasive. In some embodiments, a magnetic property to be detected may be selected from remnant magnetization, coercivity, saturation magnetization, and/or combinations thereof.

In some embodiments, a super paramagnetic particle may comprise a crystalline face centered cubic structure. A super paramagnetic particle may comprise a spinel ferrite according to some embodiments. A super paramagnetic particle may have, in some embodiments, a chemical formula $MFe_2O_4$, where M represents a transition metal (e.g., cobalt, copper, iron, magnesium, manganese, nickel, zinc, and/or combinations thereof). Cobalt, iron, oxygen, and/or combinations thereof may be desirable components of a super paramagnetic particle in some embodiments. A super paramagnetic particle may have, according to some embodiments, a generally spherical shape or a generally cuboidal shape.

According to some embodiments, MNPs and/or adsorbent materials may be contacted with and/or bind one or more of a wide variety of adsorbates. Examples of adsorbates may include, without limitation, Agent 15 (BZ), ammonia, an arsine, arsenic pentafluoride, bis(trifluoromethyl)peroxide, boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, cyclosarin (GF), diazinon, diazomethane, diborane, dichloroacetylene, dichlorosilane, dimethyl methylphosphonate (DMMP), disulfur decafluoride, fluorine, formaldehyde (gas), germane, hexaethyl tetraphosphate, hydrogen azide, hydrogen chloride, hydrogen cyanide, hydrogen selenide, hydrogen sulfide, hydrogen telluride, Lewisite (L), nickel tetracarbonyl, a nitrogen oxide (e.g., nitrogen dioxide), nitrogen mustard (HN-1, HN-2, HN-3), a Novichok agent, oxygen difluoride, pepper spray, perchloryl fluoride, perfluoroisobutylene, phosgene, phosgene oxime (CX), phosphine, phosphorus pentafluoride, pinacolyl methylphophonate (PMP), sarin (GB), selenium hexafluoride, silicon tetrachloride, silicon tetrafluoride, soman (GD), stibine, sulfur mustard (HD, H), sulfur dioxide, sulfur tetrafluoride, tabun (GA), tear gas, tellurium hexafluoride, tetraethyl dithiopyrophosphate, tetraethyl pyrophosphate, trifluoro acetylchloride, tungsten hexafluoride, VR, VX, and combinations thereof.

One or more potential references may be selected for comparison with a detected magnetic property according to some embodiments. For example, a reference may comprise at least one magnetic property of a super paramagnetic particle naïve to contact with a test fluid and/or an adsorbate. For example, a reference may comprise a super paramagnetic particle prior to its contact with a test fluid and/or an adsorbate. In some embodiments, detecting may comprise (e.g., may further comprise) detecting the magnetic property of a super paramagnetic particle prior to the contacting to form the reference. Another example of a reference may comprise a second super paramagnetic particle, identical to the first except that the second (reference) paramagnetic particle is naïve to test fluid and/or adsorbate.

According to some embodiments, the present disclosure relates to reactive self-indicating absorbent materials. For example, a reactive self-indicating absorbent material may comprise a super paramagnetic particle; and/or a semi permeable support. A super paramagnetic particle may be configured, in some embodiments, such that at least one magnetic property of the super paramagnetic particle changes upon contact with an adsorbate (e.g., one of the adsorbates listed above). According to some embodiments, the area occupied by super paramagnetic particles is coextensive with the area of the semi permeable support. A semi permeable support may comprise a fiber, a bead, a foam, a mesh, an adsorbent (e.g., an adsorbent particle) and/or combinations thereof in some embodiments. A fiber may comprise, according to some embodiments, a cellulose fibers (e.g., paper, cotton), a carbon fiber, a polyester fiber, an acrylic fiber, a glass fiber, a fiberglass fiber, an electrospun fiber, a fiber containing an adsorbent, and/or combinations thereof. Non-limiting examples of beads may include, in some embodiments, a nanoparticle, sand, silica, a glass bead, a polysaccharide bead, a resin bead, an agarose bead, a polymer bead, a carbon bead, an adsorbent bead and/or combinations thereof. An adsorbent may include, for example, one or more particles (e.g., an adsorbent particle, a bead, an extrudate, a binder-bound particle, a pressed particle, and/or combinations thereof), each capable of binding an adsorbate. In some embodiments, an adsorbent may be selected from a carbon, a zeolite, a silica, a MOF, a reticular adsorbent, a carbon nanotube, a pillard clay, a templated silica, an aluminophosphate, a silicoaluminophosphate, and/or combinations thereof.

According to some embodiments, a reactive self-indicating absorbent material may comprise a static electric charge. A semi permeable support may be configured in a layer, a bed, a cartridge, a column, and/or combinations thereof in some embodiments. One or more super paramagnetic particles may be dispersed (e.g., uniformly dispersed and/or non-uniformly dispersed) within a semi permeable support according to some embodiments. A reactive self-indicating absorbent material may comprise, in some embodiments, one or more super paramagnetic particles comprised in a layer adjacent to the semi permeable support and/or a coating adjacent to the semi permeable support.

A reactive self-indicating absorbent material may comprise, in some embodiments, a super paramagnetic particle having a crystalline face centered cubic structure and/or a super paramagnetic particle having a spinel ferrite. According to some embodiments, a reactive self-indicating absorbent material may comprise a super paramagnetic particle having a chemical formula $MFe_2O_4$, where M represents a transition metal (e.g., cobalt, copper, iron, magnesium, manganese, nickel, zinc, and/or combinations thereof). A reactive self-indicating absorbent material may comprise a super paramagnetic particle having cobalt, iron, oxygen, and/or combinations thereof in some embodiments. A super paramagnetic particle comprised in a reactive self-indicating absorbent material may have, according to some embodiments, a generally spherical shape or a generally cuboidal shape. A reactive self-indicating absorbent material may have, in some embodiments, a generally circular shape, a generally rectangular shape, or a generally annular shape.

The present disclosure relates to systems for assessing the performance and/or remaining life of a reactive self indicating adsorbent material according to some embodiments. A system may comprise, for example, a reactive self indicating adsorbent material, wherein the reactive self indicating adsorbent material comprises at least one super paramagnetic particle and a semi permeable support, wherein the at least one super paramagnetic particle is configured such that at least one magnetic property of the at least one super paramagnetic particle changes upon contact with an adsorbate; and/or at least one detector configured and arranged to detect the at least one magnetic property. In some embodiments, a system may comprise a fluid intake in fluid communication with the reactive self indicating adsorbent material and a fluid outlet in fluid communication with the reactive self indicating adsorbent material. A super paramagnetic particle may be positioned, for example, generally between the fluid intake and the reactive self indicating adsorbent material. A detector may be operable, according to some embodiments, to detect the change in a magnetic property of a super paramagnetic particle without disturbing the fluid communication between the fluid intake and the reactive self indicating adsorbent material and/or without disturbing the fluid communication between the fluid outlet and the reactive self indicating adsorbent material. In some embodiments, a system may comprise a super paramagnetic particle having a crystalline face centered cubic structure and/or a super paramagnetic particle having a spinel ferrite. A super paramagnetic particle in a system may have the chemical formula $MFe_2O_4$, wherein M represents a transition metal (e.g., cobalt, copper, iron, magnesium, manganese, nickel, zinc, and/or combinations thereof), according to some embodiments. For example, a super paramagnetic particle may comprise cobalt, iron, and oxygen and/or may have a generally spherical shape or a generally cuboidal shape. A magnetic property to be detected in a system may be selected from remnant magnetization, coercivity, saturation magnetization, and combinations thereof. A system may comprise, according to some embodiments, a super paramagnetic particle comprised in a layer adjacent to the semi permeable support or a coating adjacent to the semi permeable support.

A detector may be selected from a vector magnetometer, a scalar magnetometer (e.g., an alkali vapor scalar magnetometer), a cylindrical core magnetometer, a rotating coil magnetometer, a search coil magnetometer, a Hall effect magnetometer, an atomic magnetometer, a proton precession magnetometer, a Overhauser effect magnetometer, a fluxgate magnetometer, a caesium vapor magnetometer, a spin-exchange relaxation-free (SERF) atomic magnetometer, a SQUID magnetometer, and/or combinations thereof according to some embodiments of the disclosure. A system may comprise a processor operably linked to the at least one detector and a display operably linked to the processor. For example, a processor may be configured and arranged to compare a signal from the detector with a reference to produce an assessment of the performance and/or remaining life of the reactive self indicating adsorbent material. In some embodiments, a display may be configured and arranged to display the assessment in audible, visible, and/or tactile form.

BRIEF DESCRIPTION OF THE DRAWINGS

Some embodiments of the disclosure may be understood by referring, in part, to the present disclosure and the accompanying drawings, wherein:

FIG. 3 is a sectional view of a device having a support and a layer of MNPs on one surface of the support according to a specific example embodiment of the disclosure;

FIG. 4 is a sectional view of a device having a support and MNPs dispersed throughout the support according to a specific example embodiment of the disclosure;

FIG. 5 is an elevation view of a device having a support and a band of MNPs on one surface of the support according to a specific example embodiment of the disclosure;

FIG. 6 is a sectional view of a device having a support and a band of MNPs on one surface of the support according to a specific example embodiment of the disclosure;

DETAILED DESCRIPTION

Figure 1:
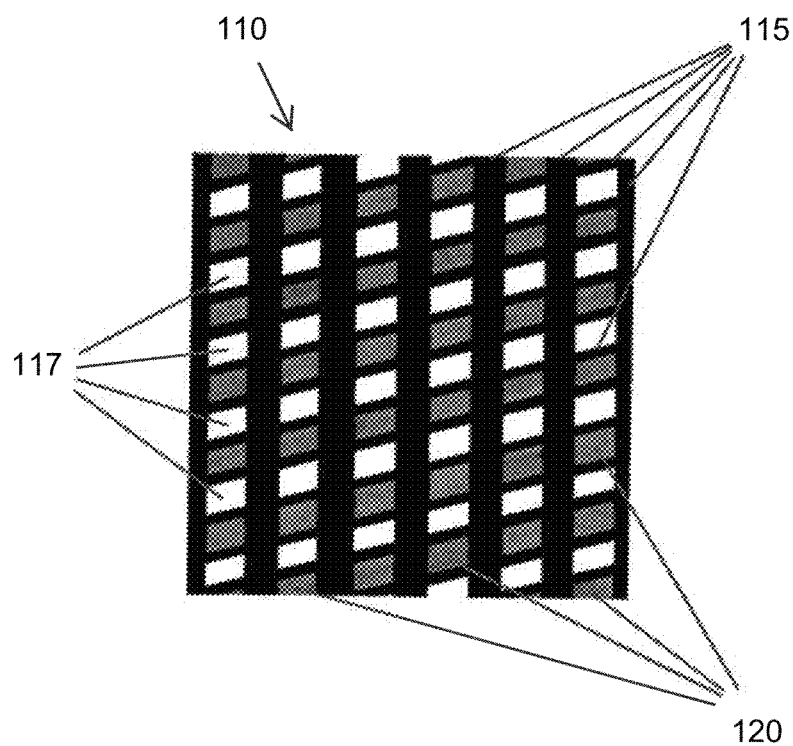
FIG. 1 illustrates a repeating metal organic framework (MOF) network according to a specific example embodiment of the disclosure.

The present disclosure relates, in some embodiments, to reactive self-indicating adsorbent materials, methods, and systems. For example, a reactive self-indicating adsorbent material may be used to indicate the performance and/or remaining life of an adsorbent material. One or more adsorption events may be associated with and/or cause a change in an adsorbent material's magnetism, in some embodiments. The nature and/or degree of change may be detected, according to some embodiments, directly, continuously and/or non-invasively. For example, a reactive self-indicating adsorbent material may provide an indication of an adsorption event occurring inside an air filter by changing its magnetism upon adsorption. In some embodiments, the nature and/or degree of change may be associated with the performance and/or remaining life of an adsorbent material (e.g., the number of additional adsorption events that the absorbent material will support before saturation and/or another undesirable event). Applications are wide ranging and include residual life indicators, chemical weapons event filtration life indicators, as well as commercial applications that utilize adsorbent filtration technologies to purify gas.

Magnetic changes upon adsorption are appealing because the magnetism of a particle may be probed without removing the particle from an engineered support. As mentioned previously, determining the remaining life of a filter (e.g., a carbon air filter) may be encumbered by a need to remove it from service. A magnetism-based method, however, may be used, in some embodiments, to determine remaining life by probing MNPs inside a filter comprising MNPs without removing the filter from its active location (e.g., a filter bank). Magnetic signals from MNPs may then provide continuous feedback to a user and/or monitor about the status of a filter (e.g., an air purification filter). For example, if a military and/or civilian item was under a chemical attack, the remaining life of protective filters may be determined, which may, in turn, permit a determination of the time the item could remain in the chemically-contaminated environment. MNPs may also be used to provide an indication of remaining adsorption bed life. Adsorption beds may be common in a variety of separations and bed life is typically only estimated, such as air filtration and water purification.

A change in magnetism upon adsorption provided by MNPs according to some embodiments of the disclosure may be a significant advantage in adsorption/filtration technology. A material that can be used as a standalone adsorbent, that also indicates its residual capacity as a result of exposure to adsorbates, has many potential applications in filtration because it may allow the user to have a quantifiable understanding of the amount of capacity that remains in a filter. For example, these materials could be incorporated into existing filters to indicate how much filtration capacity is available in a gas filter after being exposed to battle field contaminates, toxic industrial chemicals (such as ammonia or sulfur dioxide), and/or chemical warfare agents simply by monitoring the magnetism changes of the filter. Furthermore, materials may be used to indicate remaining filter life as toxic materials are being removed from a process stream in industrial applications.

Compositions

A reactive self-indicating adsorbent material, according to some embodiments, may comprise one or more super paramagnetic nanoparticles (MNPs). Significant effort has been devoted to the development of novel adsorbent materials, such as metal organic frameworks (MOFs), zeolitic imidazolate frameworks, covalently bonded organic frameworks, and engineered carbons. These materials represent a departure from amorphous adsorbents to crystalline materials that may be engineered at a molecular level to impact gas adsorption performance. Magnetic nanoparticles (MNPs) are of particular interest in this regard because MNPs have many desirable physical characteristics. Specifically, in some embodiments, MNPs may be crystalline face centered cubic structures (e.g., spinel ferrites), may contain transition metals with a chemical formula $MFe_2O_4$, and/or may be small enough in diameter to have significant surface area for adsorption (e.g., less than or equal to about 100 nm, less than or equal to about 50 nm, less than or equal to about 25 nm, less than or equal to about 10 nm, and/or less than or equal to about 5 nm). In some embodiments, M may comprise Co, Cu, Fe, Mg, Mn, Ni, or Zn. An MNP may comprise, for example, iron and cobalt (e.g., $CoFe_2O_2$). According to some embodiments, the shape of MNPs may be configured as desired and/or required. For example, $CoFe_2O_2$ MNPs may be spherical or cuboidal. Control over the topology of nanoparticles is noteworthy because the nano-edges of these materials may present unique reaction chemistry towards adsorbates in some embodiments. Particle size and/or surface area may impact, in some embodiments, performance of a material.

Metal oxide MNPs may be thermally robust and chemically stable. A surface of MNPs may be chemically modified to include specific organic functionalities, which allows MNP to be linked onto other molecules and/or chemical networks.

The surface of the spinel ferrite nanoparticles may be modified by covalently attaching a variety of organic molecules to the particles in some embodiments. For example, a functional group for linking a molecule to nanoparticles is carboxyl, R—COOH; however, other functional groups also bind to the surface. Functional groups may also be introduced onto organic ligands that have already been attached onto a nanoparticle surface. Such flexibility allows magnetic nanoparticles to be modified and utilized as nanoscale building blocks to engineer the functionality of adsorbent. For example, magnetic nanoparticles comprised of $Fe_3O_4$ may be assembled into a porous structure. Carboxyl groups may decorate the surface of adsorbent particles to provide an organic support structure to allow for the surface area of the magnetic particles to be fully accessible.

Magnetic nanoparticles may have magnetic domains that randomly flip, which results in no net magnetic properties. However, when placed in a magnetic field magnetic domains of a material may become organized and the material may become super paramagnetic.

MNPs may change their magnetic properties upon loading with para-substituted benzoic acids and substituted benzene ligands according to some embodiments. Specifically, 4 nm $MnFe_2O_4$ particles exhibit a decrease in coercivity ranging from approximately 25-50% depending on the ligand loaded, and an increase in the saturation magnetization with ligand loading. The adsorption of ligands on the MNP surface is interesting because the majority of adsorbent materials do not exhibit a change in their magnetic properties upon adsorption. However, the application of MNPs as adsorbent materials has not been examined prior to the instant application.

In some embodiments, magnetism of particles may change (e.g., significantly) upon adsorption of sulfur dioxide and organo-phosphate chemicals, such as GB simulant dimethyl methylphosphonate, Soman hydrolysis product inacolyl methylphosphonate (PMP), and Diazinon. It is important to note that MNPs are not intended as an event indicator, but rather would provide an indication of the degree of filter contamination and residual filter capacity as a result of adsorption events occurring from either battle field contamination or chemical attacks.

MNPs are attractive gas phase absorbents, at least in part, because of their adsorption of ligands in solution, the organization of transition metals in a crystal structure, and/or their unique magnetic properties. In some embodiments, adorption of sulfur dioxide on $Fe_2CoO_4$ spinel ferrite nanoparticles and/or magnetic changes that may occur upon adsorption may be evaluated. Sulfur dioxide may provide a good representative adsorbate probe because it has been examined on a variety of materials including carbons, graphite, MOFs, inorganic materials, as well as composite materials.

In some embodiments, a reactive self-indicating adsorbent material may adsorb more (e.g., ~1.5×, ~2×, ~3×, ~5× or more) adsorbate than activated carbon (e.g., on a volume and/or weight basis). For example, a reactive self-indicating adsorbent material may adsorb more $SO_2$ as activated carbon on a per volume basis. Adsorption studies elaborated in the Examples below have revealed that a specific example embodiment of a material adsorbed twice as much $SO_2$ as activated carbon on a per volume basis. Adsorption of $SO_2$ is particularly appealing because it is a common battlefield contaminant that accumulates in filters and reduces filter life. These Examples provide strong support for the use of MNPs as a residual life indicator which quantitatively detail how much life remains in a filter that has been exposed to battle field contaminants.

A reactive self-indicating adsorbent material may have, according to some embodiments, both a high capacity for adsorbate (e.g., higher than carbon and/or traditional sorbents) and/or a capacity for quantifiable changes in their magnetic properties (e.g., to support direct, continuous and/or non-invasive detection).

Devices

The present disclosure relates, in some embodiments, to devices comprising one or more MNPs. For example, a device may be configured as a filter. A device may include, in some embodiments, a semi permeable support and one or more MNPs. According to some embodiments, a semi permeable support may be configured to permit passage of some materials (e.g., solid, liquid, and/or gaseous) and bind, trap, and/or otherwise resist and/or deny passage of others (e.g., toxins, chemical warfare agents, dust, allergens, and/or combinations thereof). Examples of a semi permeable support may include, without limitation, a filter, a web, a bed, a matrix, and/or combinations thereof.

In some embodiments, a semi permeable support may comprise any semi-permeable barrier including, for example, fibers (e.g., of a woven or nonwoven fabric), particles and/or beads (e.g., in a fluidized bed, a solid bed, and/or other bed), foams, wire mesh, solid particles or powders in a fabric, powders, and/or combinations thereof. Non-limiting examples of fibers may include, in some embodiments, cellulose fibers (e.g., paper, cotton), carbon fibers, polyester fibers, acrylic fibers, glass fibers, fiberglass fibers, electrospun fibers, and/or combinations thereof. Non-limiting examples of beads may include, in some embodiments, nanoparticles (e.g., MNPs), sand, silica (e.g., diatomaceous earth), glass beads, polysaccharide beads (e.g., Sepharose®), resin beads, agarose beads, polymer beads, carbon beads, adsorbent beads, and/or combinations thereof. A support (e.g., a matrix) may comprise a static electric charge, in some embodiments. A support may be arranged in any desirable and/or required structure according to some embodiments. For example, a support may be arranged in a membrane, a layer, a bed, a cartridge, and/or a column. According to some embodiments, one or more MNPs may be dispersed (e.g., uniformly, non-uniformly, randomly, haphazardly) within a support. One or more MNPs may be, instead or in addition, adjacent to and/or contacted with a semi permeable support surface (e.g., as a coating or layer). It may be desirable in some embodiments to interpose a coating and/or layer between MNPs and a matrix.

MNPs may be combined with a support in any manner desired or required. For example, a device may comprise a support with one or more MNPs integrated and/or intermixed therein. A device may comprise a support with a coating comprising one or more MNPs. A device may comprise one or more MNPs forming a first layer and an active support forming a second layer and performing the actual filtration. In some embodiments, one or more MNPs may be positioned closer to the upstream surface (e.g., a surface contacted by naïve adsorbate earlier than another surface), closer to the downstream surface (e.g., a surface contacted by naïve adsorbate later than another surface), or uniformly distributed (e.g., in 1, 2, and/or 3 dimensions). A device may comprise, for example, a support coated on at least a portion of an upstream surface with a composition comprising MNPs. Coatings and/or layers may be configured, according to some embodiments, in any desirable pattern. For example, a coating and/or layer may have a perimeter defined by any regular or irregular geometric shape. The size and shape of a coating and/or layer may be selected, according to some embodiments, to minimize and/or obviate any potential impact on performance of a device. For example, a coating may be applied in strips, grids, and/or spokes to permit magnetic detection without impacting flow through a support. In some embodiments, a coating and/or layer may be or may not be coextensive with respect to an adjacent support. Coating only a portion of a support may lead to desirable cost savings and/or ease of manufacturing, in some embodiments.

A support may have any desired size and/or shape according to some embodiments. For example, a support may be configured and arranged as a generally rectangular filter, a generally circular filter, and/or a generally annular filter. In use, a material (e.g., an actual and/or suspected contaminated fluid) may be directed to an inner surface of an annular filter and permitted to pass through the filter radially. A support may be configured to have, in some embodiments, a thickness sufficient to perform (e.g., a filtration function and/or a support function to accommodate MNPs adequate to produce a detectable signal). According to some embodiments, a device may comprise MNPs in the absence of a support. A bed of MNPs, for example, may function both as a semi permeable matrix and a reactive self-indicating adsorbent material.

A reactive self-indicating adsorbent material, according to some embodiments, may comprise one or more adsorbent support materials with at least one MNP (e.g., embedded in the adsorbent). For example, an adsorbent material may be designed and configured to target (e.g., selectively target) a particular absorbate gas. In some embodiments, an adsorbent material may be custom made to contain specific organic functionalities or metals to tailor the adsorbent material to target one or more specific adsorbates. For example, pore size may be controlled during synthesis to selectively allow molecules to pass through the channels of the material and/or a variety of functional groups may be introduced in the walls of the channels to enhance adsorption. According to some embodiments, a metal organic framework (MOF) may be selected as an adsorbent to which MNP indicators may be added. For example, MOF links may be customized to accept MNPs and a network of MNP sites may be added to the material. A specific example embodiment of a MOF network is shown in FIG. 1, which illustrates a well defined structure and clearly defined porosity. As shown, reactive self-indicating adsorbent material 110 comprises MOF network 115, pores 117, and MNPs 120. Other adsorbents such as activated carbons may also be modified to accept MNPs.

Figure 2:
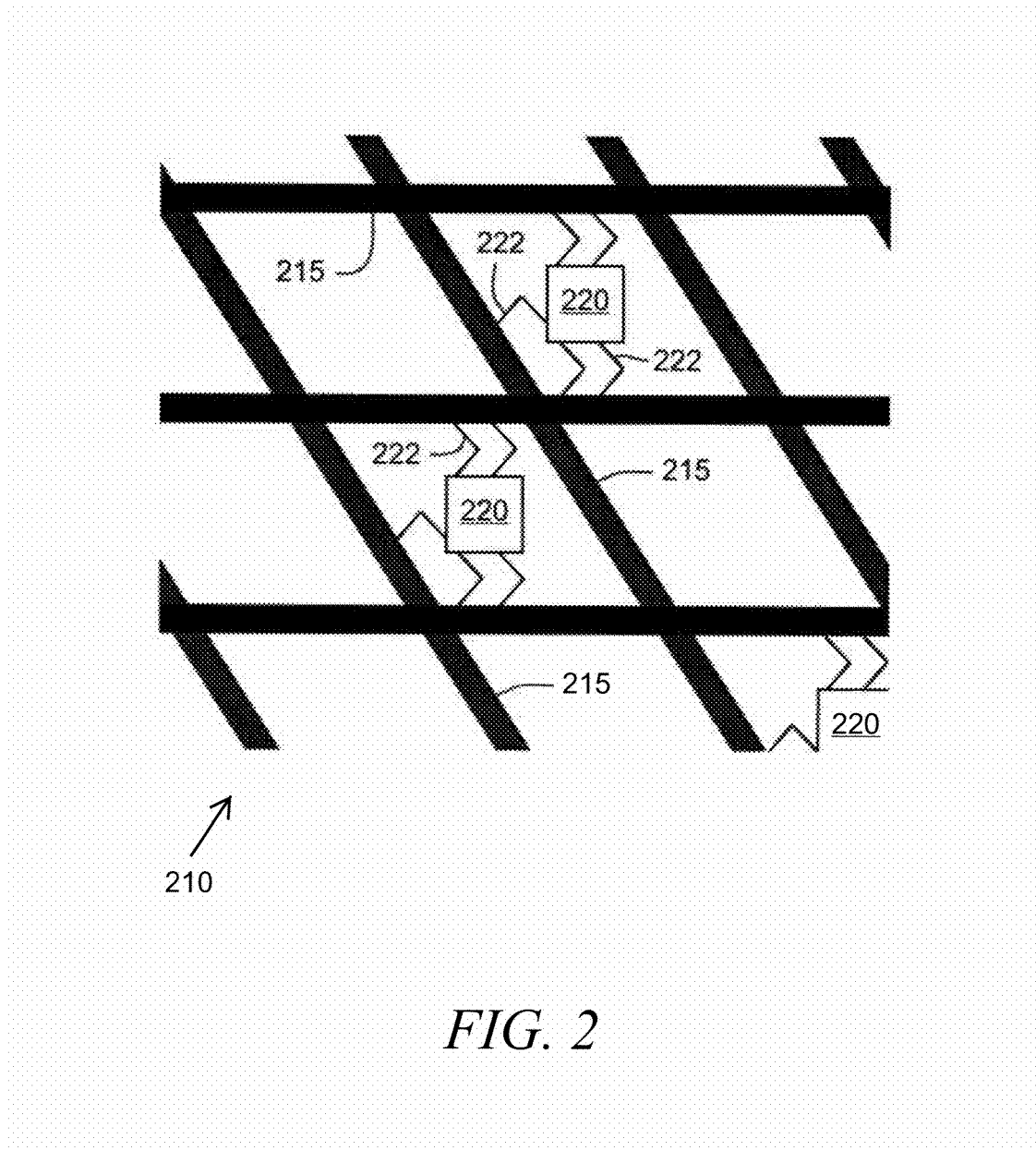
FIG. 2 illustrates MNPs integrated and chemically bound in a MOF network according to a specific example embodiment of the disclosure.

A device may comprise, in some embodiments, hybrid network adsorbents comprising nanoparticles embedded in adsorbent materials. For example, crystalline adsorbents embedded with nanoparticles that have a change in their physical properties upon adsorption may contain an indicator of when adsorption has occurred. In some embodiments, a multifunctional composite adsorbent material may comprise at least one MNP and/or at least one MOF. A MOF material may comprise, according to some embodiments, one or more MNPs and/or the MOF adsorbent has an intrinsic adsorption capacity indicator. A MNP may be integrated into a network of MOFs by functionalizing a surface of the MNPs with MOF links or structural building units (SBUs) and then growing a MOF network around the MNP in some embodiments. A MNP may be integrated into a network of MOFs, according to some embodiments, by directly integrating MNPs by including MNPs in the reaction solution during the MOF synthesis. These mechanisms may allow development of a composite structure 210 as shown in FIG. 2, where MNP 220 is surrounded by a network of porous adsorbent MOF material 215. FIG. 5 shows the carboxyl functional groups of organic linkers 222 binding to the surface of MNP 220 and anchoring MNP 220 in MOF network 215. The success of such an approach may have a broad impact because nanoparticle-based reaction centers allow a variety of physical and chemical activities to be incorporated into MOF networks.

A device, in some embodiments, may comprise one or more catalysts, enzymes, oxidizers, zeolites and/or combinations thereof capable of chemically reacting with at least one adsorbate. For example, a device may include a material capable of converting a dangerous adsorbate into a safer physical and/or chemical form.

Figure 7:
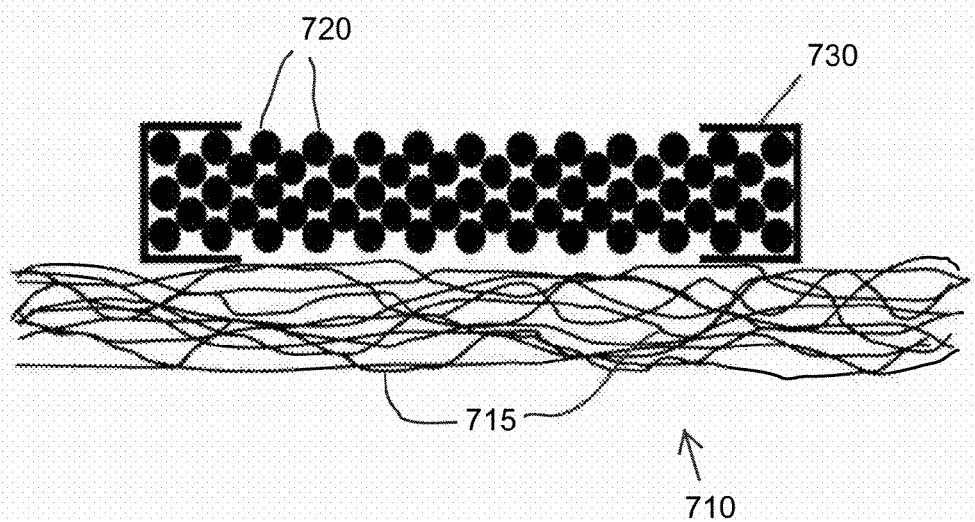
FIG. 7 is a sectional view of a device having a housing filled with MNPs adjacent to an adsorbent material according to a specific example embodiment of the disclosure.
Figure 8:
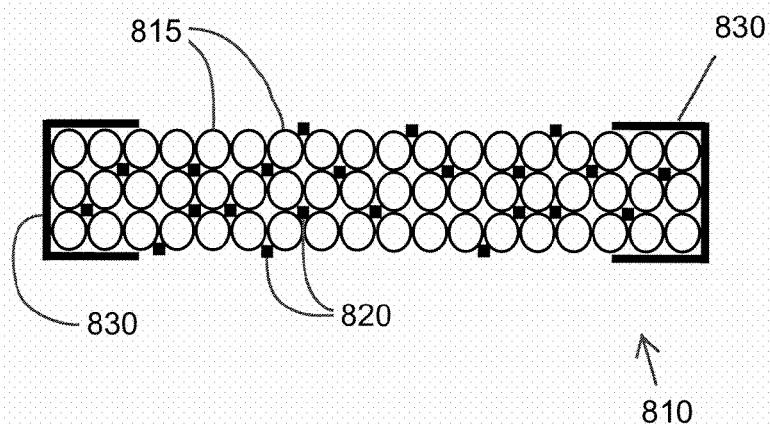
FIG. 8 is a sectional view of a device having support beads interspersed with MNPs according to a specific example embodiment of the disclosure.

FIG. 3 illustrates device 310 according to a specific example embodiment of the disclosure. As shown, device 310 includes semi permeable support 315 and coating or layer 325 comprising MNPs 320. In some embodiments, a fluid (e.g., air) may flow from left to right or from right to left through device 310. FIG. 4 illustrates device 410 according to a specific example embodiment of the disclosure. As shown, device 410 includes semi permeable support 415 and MNPs 420 dispersed therein. In some embodiments, a fluid (e.g., air) may flow from left to right or from right to left through device 410. FIG. 5 illustrates device 510 according to a specific example embodiment of the disclosure. As shown, flat, rectangular device 510 includes housing 530 and MNPs arranged in bands 525 that span support 515. FIG. 6 illustrates device 610 according to a specific example embodiment of the disclosure. As shown, annular device 610 includes housing 630 and MNPs arranged in bands 625 that span support 615. A fluid (e.g., air) may flow, according to some embodiments radially outwardly or radially inwardly through device 610. FIG. 7 illustrates device 710 according to a specific example embodiment of the disclosure. As shown, device 710 includes housing 730 and MNPs 720 arranged in a bed. Support 715 may be separate from device 710 as shown here. A fluid (e.g., air) may flow, according to some embodiments, from top to bottom through device 710. FIG. 8 illustrates device 810 according to a specific example embodiment of the disclosure. As shown, device 810 includes housing 830 holding beads 815 with interspersed MNPs 820. A fluid (e.g., air) may flow, according to some embodiments, from top to bottom through device 810.

Systems

The present disclosure relates, in some embodiments, to systems comprising one or more MNPs. For example, a system may comprise one or more MNPs, a support, a housing (e.g., a filter housing), a sensor and/or detector (e.g., configured and arranged to monitor the physical integrity of a filter), a magnetometer (e.g., configured and arranged to detect changes in one or more magnetic properties of an MNP), and/or combinations thereof. For example, a system may comprise one or more MNPs, a support containing the one or more MNPS, and a magnetometer in magnetic communication with the one or more MNPs (or a portion thereof). In some embodiments, any device configured and arranged to detect magnetic fields and/or changes therein (e.g., a magnetometer) may be included in a system. For example, a magnetometer may comprise a vector magnetometer, a scalar magnetometer (e.g., an alkali vapor scalar magnetometer), a cylindrical core magnetometer, a rotating coil magnetometer, a search coil magnetometer, a Hall effect magnetometer, an atomic magnetometer, a proton precession magnetometer, a Overhauser effect magnetometer, a fluxgate magnetometer, a caesium vapor magnetometer, a spin-exchange relaxation-free (SERF) atomic magnetometer, a SQUID magnetometer, and/or combinations thereof. One or more magnetometers may be included in a system, for example, to improve signal detection.

A magnetometer may be operably linked to a power source, a processor, a memory, a display, and/or an alarm, according to some embodiments. For example, a system may be configured to indicate the performance and/or remaining life of an adsorbent material, for example, through a display (e.g., a graphic user interface, indicator light(s), and/or alarm(s)). A display may present information (e.g., an assessment) in visual form, audible form, tactile form, and/or combinations thereof. A processor may be configured to receive one or more signals from a detector (e.g., a magnetometer) and compare the received signal(s), or one or more attributes thereof, to a reference.

Figure 9:
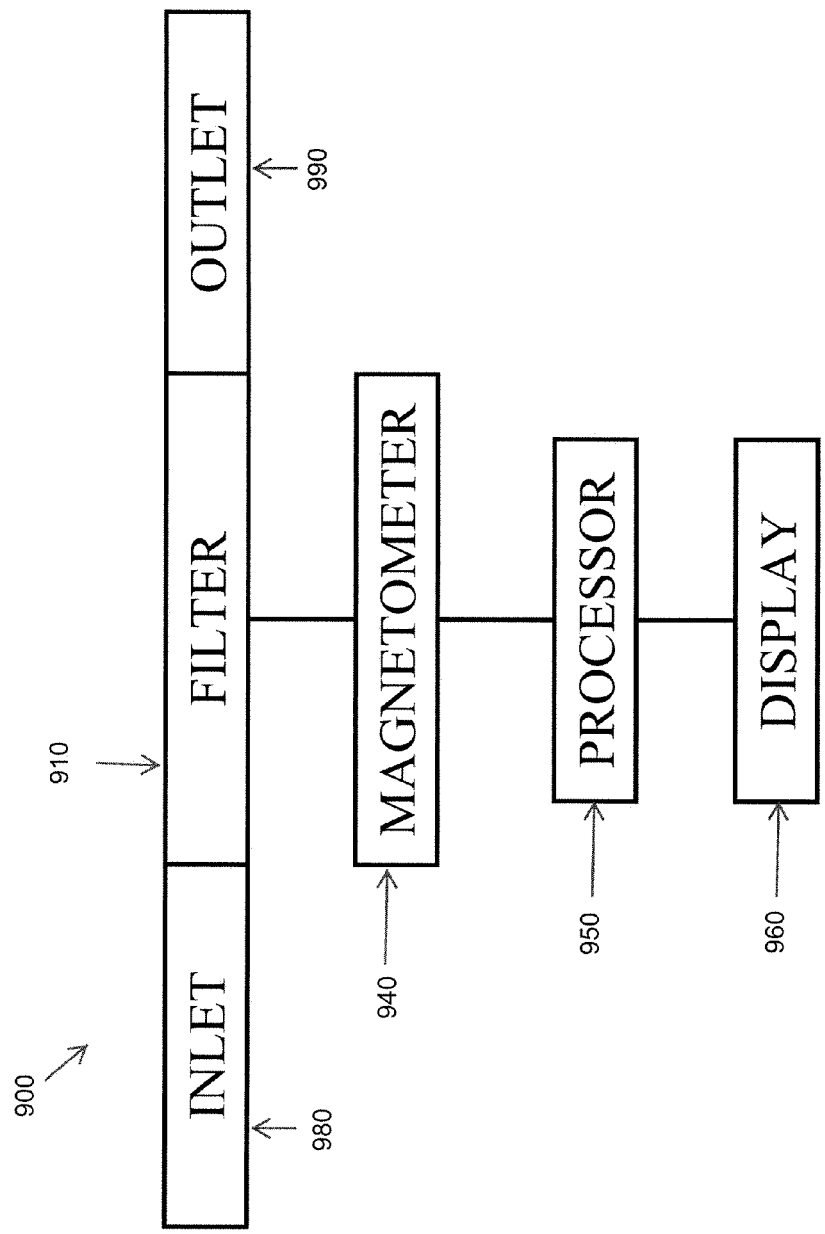
FIG. 9 illustrates a system for assessing the performance and/or remaining life of an adsorbent material according to a specific example embodiment of the disclosure.

FIG. 9 illustrates system 900 for assessing the performance and/or remaining life of an adsorbent material according to a specific example embodiment of the disclosure. As shown, system 900 includes fluid inlet 980, filter 910, and fluid outlet 990, in fluid communication with each other, respectively. System 900 also includes detector 940 in magnetic communication with filter 910, processor 950 operably linked to detector 940, and display 960 operably linked to processor 950. Processor 950 may be configured to receive one or more signals from detector 940, compare one or more attributes of the signal to a reference, and assess performance and/or remaining life of filter 910. Processor 950 may be configured to present one or more aspects of the assessment on display 960 (e.g., a metric of performance, fraction of filter life remaining, and/or an alarm when performance and/or remaining life fall before a desired threshold).

Figure 10:
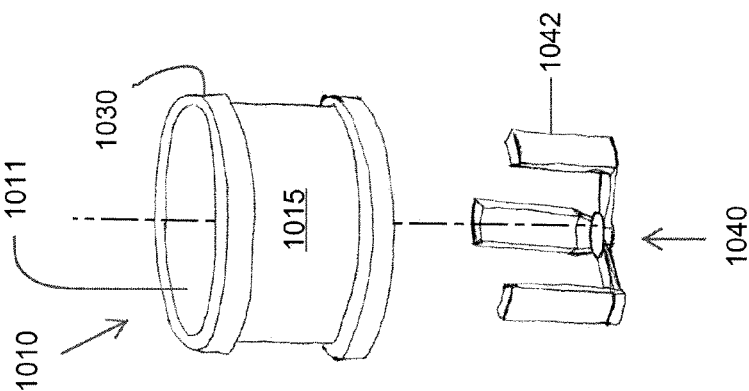
FIG. 10 is an isometric view of an annular filter cartridge and associated magnetometer assembly according to a specific example embodiment of the disclosure.

FIG. 10 illustrates annular filter cartridge 1010B and associated detector assembly 1040 according to a specific example embodiment of the disclosure. Annular filter cartridge 1010 may comprise one or more MNPs homogenously distributed throughout support 1015 or arranged in bands 1025. As shown, detector assembly 1040 may be configured to be inserted (e.g., removably inserted) in aperture 1011, defined by cartridge 1010, and position probes 1042 adjacent to support 1015. In some embodiments, for example, where MNPs are arranged in bands 1025, cartridge 1010 and/or detector assembly 1040 may be configured such that when detector assembly 1040 is inserted into aperture 1011, bands 1025 and probes 1042 are adjacent (e.g., immediately adjacent) to one another.

Figure 11:
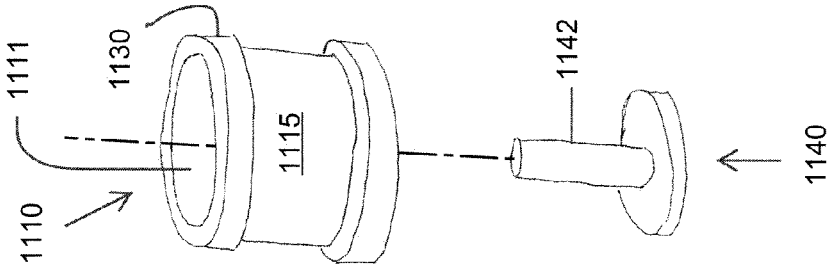
FIG. 11 is an isometric view of an annular filter cartridge and associated magnetometer assembly according to a specific example embodiment of the disclosure.

FIG. 11 illustrates annular filter cartridge 1110 and associated detector assembly 1140 according to a specific example embodiment of the disclosure. Annular filter cartridge 1110 may comprise one or more MNPs homogenously distributed throughout support 1115 or arranged in bands 1125. As shown, detector assembly 1140 may be configured to be inserted (e.g., removably inserted) in aperture 1111, defined by cartridge 1110, and position probe 1142 adjacent to support 1115. The size of probe 1142 and/or the diameter of cartridge 1110 may be adapted as needed and/or desired to permit detection of magnetic changes at or in cartridge 1110.

Figure 12:
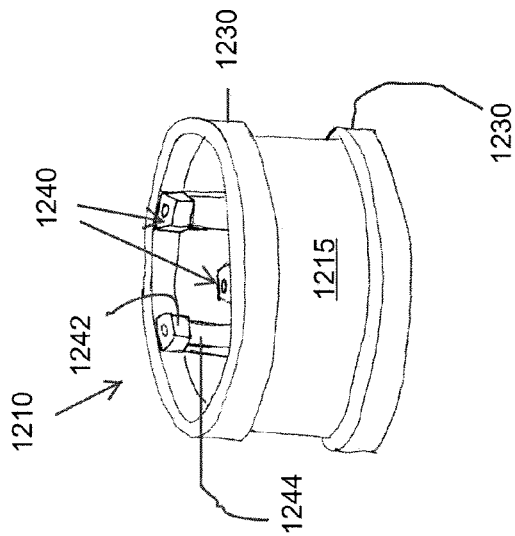
FIG. 12 is an isometric view of an annular filter cartridge with an integral magnetometer assembly according to a specific example embodiment of the disclosure.

FIG. 12 illustrates annular filter cartridge 1210 with integral detector 1240 according to a specific example embodiment of the disclosure. Probes 1242 may be configured an arranged to include connectors and/or ports to support wired or wireless connection to processor 1250.

Methods of Use

The present disclosure relates, in some embodiments, to methods for detecting and/or monitoring (e.g., assessing) the performance and/or remaining life of an adsorbent material directly, continuously and/or non-invasively. For example, a method may comprise contacting a composition to be filtered with an adsorbent material and monitoring one or more magnetic properties of the adsorbent material. A composition to be filtered may comprise a fluid (e.g., a liquid and/or a gas) and/or a solid (e.g., in powder, particulate, and/or granular form). Examples of fluids may include, according to some embodiments, air, (e.g., ambient air, building HVAC intake air, vehicle intake air), an industrial exhaust gas, jet fuel, heavy diesel, water, an industrial process stream of chemicals being filtered, closed system air (a space craft or submarine), materials being processed by thermal swing or pressure swing adsorption (regenerable fixed-beds for air generation/purification, chemical processing), hydrogen, adsorption refrigeration chemicals, mercury, and/or combinations thereof.

The present disclosure relates, according to some embodiments, to methods for selecting and/or establishing a metric of performance and/or remaining life of an adsorbent material. For example, a method may comprise contacting a first side of an adsorbent material with a metered amount of an adsorbate and/or observing (a) amount of adsorbate on a proximal side of the adsorbent material, (b) amount of adsorbate on a distal side of the adsorbent material, and/or (c) any change in magnetism. A metered amount of an adsorbate may comprise a measured amount (e.g., volume and/or mass) of adsorbate per unit adsorbate delivery vehicle (e.g., volume and/or mass) and/or per unit adsorbent (e.g., volume and/or mass) in some embodiments. A metered amount of an adsorbate may comprise, according to some embodiments, delivery of a measured amount (e.g., volume and/or mass) of adsorbate in a single pulse, two or more pulses, intermittently, and/or continuously over time to a proximal side of an adsorbent material. In some embodiments, selecting and/or establishing a metric of performance and/or remaining life of an adsorbent material may comprise, for example, correlating a change in magnetism and/or rate of change in magnetism with a desired (a) amount of adsorbate on a proximal side of an adsorbent material, (b) rate of adsorbate disappearance on a proximal side of an adsorbent material, (c) amount of adsorbate on a distal side of an adsorbent material, (d) rate of adsorbate appearance on a distal side of an adsorbent material, and/or combinations thereof. Selecting and/or establishing a metric of performance and/or remaining life of an adsorbent material may comprise, in some embodiments, determining a point at which an adsorbent material may be considered exhausted. Exhaustion may be defined as required or desired depending on the application, in some embodiments. Exhaustion, for example, may correspond to adsorption of a threshold fraction (e.g., more than about 95%, more than about 98%, more than about 99%, and/or about 100%) of the theoretical and/or empirically-determined maximum amount of adsorbate for a given adsorbent material. Selecting and/or establishing a metric of performance and/or remaining life of an adsorbent material may be dynamic in that it may take account of one or more changing parameters such that an appropriate and/or desired metric is selected and/or established.

At least one magnetic property of an MNP may change upon contact with an adsorbate of interest in some embodiments. MNPs may be designed and/or selected, in some embodiments, to interact with any adsorbate of interest. For example, an adsorbate may comprise an organic chemical, an inorganic chemical, and/or combinations thereof. An adsorbate, according to some embodiments, may be a solid, a liquid, and/or a gas. In some embodiments, an adsorbate may be comprised in a fluid (e.g, a gas and/or a vapor). According to some embodiments, an adsorbate may be selected from the group consisting of a chemical warfare agent (CWA), a chemical warfare simulant, a toxic gas (e.g., a highly toxic gas), a noxious gas, an herbicide, an insecticide, an algaecide, a fungicide, a fluorocarbon, a chlorofluorocarbon, a toxic industrial chemical (TIC), a battlefield contaminant (BFC), and/or combinations thereof. Examples of an adsorbate may include, according to some embodiments, Agent 15 (BZ), ammonia, an arsine, arsenic pentafluoride, bis(trifluoromethyl)peroxide, boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, cyclosarin (GF), diazinon, diazomethane, diborane, dichloroacetylene, dichlorosilane, dimethyl methylphosphonate (DMMP), disulfur decafluoride, fluorine, formaldehyde (gas), germane, hexaethyl tetraphosphate, hydrogen azide, hydrogen chloride, hydrogen cyanide, hydrogen selenide, hydrogen sulfide, hydrogen telluride, Lewisite (L), nickel tetracarbonyl, a nitrogen oxide (e.g., nitric oxide, nitrogen dioxide), nitrogen mustard (HN-1, HN-2, HN-3), a Novichok agent, octane, oxygen difluoride, parathion, pepper spray, perchloryl fluoride, perfluoroisobutylene, phosgene, phosgene oxime (CX), phosphine, phosphorus pentafluoride, pinacolyl methylphophonate (PMP), sarin (GB), selenium hexafluoride, silicon tetrachloride, silicon tetrafluoride, soman (GD), stibine, sulfur mustard (HD, H), sulfur dioxide, sulfur tetrafluoride, tabun (GA), tear gas, tellurium hexafluoride, tetraethyl dithiopyrophosphate, tetraethyl pyrophosphate, trifluoro acetylchloride, tungsten hexafluoride, VR, VX, and/or combinations thereof. An adsorbate may comprise, for example, sulfur dioxide and organo-phosphate chemicals, such as GB simulant dimethyl methylphosphonate, Soman hydrolysis product pinacolyl methylphosphonate (PMP), and Diazinon (e.g., O,O-Diethyl O-[4-methyl-6-(propan-2-yl)pyrimidin-2-yl] phosphorothioate)).

Battle field contaminates (BFCs) may include, in some embodiments, one or more chemicals that may be common on a battlefield, but not necessarily chemical agents used as weapons. Some of these materials may not be particularly toxic. Examples of BFCs may include, for example, fuel (e.g., gasoline, kerosene, diesel, and/or jet fuel), fuel combustion products, fuel vapors (e.g., hydrocarbons from fuel evaporation), heavy organics, acids (e.g., sulfuric and/or hydrochloric acid), combustion products of rubber, plastics, metals, wire, and other materials released from burning vehicles, buildings, munitions, crude oil, and the like. These chemicals may be readily adsorbed and/or removed by air filters. Removing these chemicals from air may reduce filter capacity. The exact reduction in filter capacity may not be known such that filters may have to be pulled out of service and probed to determine if they need changed. Filters may be changed as a result of ageing effects in the filter that occur as a result of these adsorption events. Ageing events may reduce the reactive capacity of a filter. Although the physical capacity for adsorption may still be high, the reactive ability of the filter to destroy chemical threats may be reduced, therefore filters may be changed all the time to prevent any chance of threats. According to some embodiments, reactive, self-indicating adsorbent materials may facilitate more efficient, more timely, and/or more accurate determinations of when a filter needs to be changed.

In some embodiments, the amount of adsorbate required to saturate a detector may exceed (e.g., far exceed) the amount of adsorbate required to saturate an associated semi permeable support. This may ensure, for example, that the detector does not prematurely indicate filter failure. MNPs may be designed, manufactured, and/or selected to have adsorbate adsorption and/or desorption profiles that are similar to the adsorbate adsorption and/or desorption profiles of the semi permeable support.

Performance of an adsorbent material may be assessed, according to some embodiments, by positioning at least one MNP and/or a detector downstream of the adsorbent material and monitoring the appearance of adsorbate at the at least one MNP. Little or no adsorbate may be detected initially, but may increase as time passes (e.g., filtration continues). A detector may be calibrated, for example, by correlating at least one magnetism metric with another detection method (e.g., gas chromatography, mass spectrometry, and/or combinations thereof).

Assessing remaining life of an adsorbent material may include, according to some embodiments, positioning at least one MNP and/or a detector within and/or upstream of the adsorbent material and monitoring the appearance of adsorbate at the at least one MNP. Assessing the performance and/or remaining life of an adsorbent material may be pressure insensitive, according to some embodiments. For example, contacting a reactive self-indicating adsorbent material with a fluid (e.g., comprising or potentially comprising an adsorbate) may be performed at ambient pressure, lower than ambient pressure, or higher than ambient pressure. In some embodiments, assessing the performance and/or remaining life of an adsorbent material may take place within ordinary operation parameters (e.g., temperature, pH, pressure, flow rate, surface area, and/or combinations thereof) of an adsorbent material (e.g., filter).

Manufacturing Methods

The present disclosure relates, in some embodiments, to methods for preparing a nanoparticle (e.g., an MNP). A variety of methods to synthesize high quality $CoFe_2O_4$, $MnFe_2O_4$ and other magnetic spinel ferrite nanoparticles have been developed. MNPs comprising, for example, $CoFe_2O_2$ may be prepared using a micelle synthesis method.

The present disclosure relates, in some embodiments, to methods for preparing a reactive self-indicating adsorbent material. For example, a reactive self-indicating adsorbent material may be prepared by coating (e.g., wash coating) one or more MNPs onto a support. In some embodiments, a device may be prepared by layering one or more MNPs onto a support (e.g., carbon fiber). Filters may be prepared using a form to contain adsorbent particles and/or powders. Adsorbent material may be placed into a filter to ensure that the bed is packed, which may reduce and/or prevent fluid from channeling and/or by-passing adsorbent particles. Filters may be prepared to ensure that each filter has a consistent particle size, adsorbent packing, and/or adsorbent mass. Layered filters may be prepared similarly with two different filter filing steps. The layers may, or may not, be separated by a screen to hold the layers in place. Adsorbent particles may be engineered, in some embodiments, with a binder (e.g., to ensure that the particles are hard enough not to dust or produce fines). A binder may be selected from a variety of materials depending on the adsorbent. Binders may include, for example, resins, pitch, tar, plastics, inorganic powders or other blends, and/or combinations thereof. MNPs may be added at any of these processing steps to incorporate the particles into a filter. For example, the screens that support the carbon may be dip coated with a fluid to leave MNPs dried on the surface of the screen. MNPs may be simply added to bulk powder prior to the powder being bound into particles. MNPs may be added to the binder solution in some embodiments. MNPs may be washed onto the carbon powder, or carbon particle, for example, prior to being placed into the filter.

MNPs (e.g., from an exhausted filter) may be reused, for example by treating the MNPs with a base (e.g., NaOH bath) in some embodiments. If desired and/or required, MNPs may be baked at a temperature sufficient to destroy organics deposited thereon (e.g., before, during, and/or after a base wash).

As will be understood by those skilled in the art who have the benefit of the instant disclosure, other equivalent or alternative compositions, devices, methods, and systems for detecting and/or monitoring (e.g., assessing) the performance and/or remaining life of an adsorbent material can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the chemical composition, size, shape, surface functionality, position and/or number of MNPs, the position and/or number of supports, and/or the position and/or number of detectors (e.g., magnetometers) may be varied. In some embodiments, reactive self-indicating adsorbent materials, devices (e.g., filters), detectors (e.g., magnetometers) and/or systems may be interchangeable. Interchageability may allow adsorbate sensitivity and/or specificity to be custom adjusted (e.g., by choosing appropriate MNP(s) and/or detector(s)). In addition, the size of a device and/or system may be scaled up (e.g., for use in large-volume air filtration systems such as building HVAC systems) or down (e.g., for use in small-volume air filtration systems such as a tank or a chemical fume hood) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/−about 10%, depicted value +/−about 50%, depicted value +/−about 100%) and/or a range endpoint. With respect to the former, a value of 50 depicted in an example, table, and/or drawing may form the basis of a range of, for example, about 45 to about 55, about 25 to about 100, and/or about 0 to about 100. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

All or a portion of a device and/or system for detecting and/or monitoring (e.g., assessing) the performance and/or remaining life of an adsorbent material may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein.

Example 1

Materials Synthesis $CoFe_2O_4$ MNPs were made using a microemulsion by mixing $CoCl_2.6H_2O$ and $FeCl_2.4H_2O$ in aqueous solution containing sodium dodecyl sulfate (SDS). The mixture was then heated to approximately 70° C. in a heating mantle for approximately 30 minutes. An aqueous solution of 40% methylamine was then added to precipitate the particles. The solution was then allowed to stir overnight and the particles were collected by centrifugation, washed with methanol, and collected by centrifugation. The particles were dried at 110° C. The particles were then washed in a bath of 10 M sodium hydroxide to remove any remaining surfactant from synthesis. These particles were used in the $SO_2$ detection/filtration experiments described below.

Example 2

Micro-Breakthrough Experiments

Figure 13:
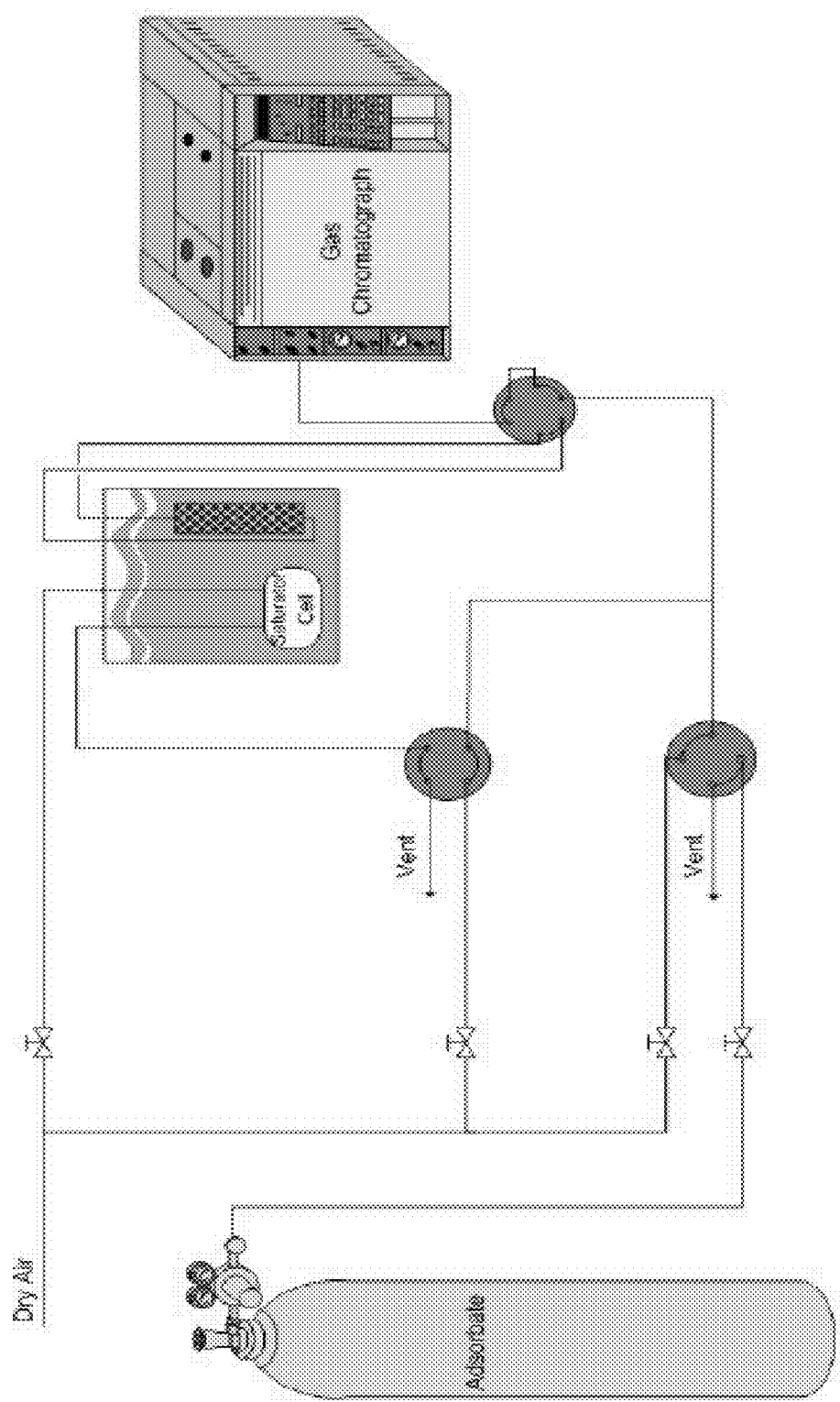
FIG. 13 illustrates a breakthrough system utilized for adsorption tests according to a specific example embodiment of the disclosure.

Micro-breakthrough experiments were conducted using the apparatus shown in FIG. 13. Analyte was injected into a ballast and subsequently pressurized; this chemical mixture was then mixed with an air stream to achieve a predetermined concentration. For this set of tests the challenge concentration was fixed at 1000 mg/m³. The completely mixed stream then passed through a sorbent bed submerged in a temperature-controlled water bath. The sorbent bed is filled on a volumetric basis in a 4 mm internal diameter tube to a height of 4 mm resulting in an average of 57 mg of MNP material being used for each test. The sample bed was constructed of glass so that the bed height could be measured. The samples were tested without out-gassing or regeneration. To evaluate the desorption behavior of the material after breakthrough had occurred clean air, with the humidity of the clean air matching the conditions of the experiment, was passed to the bed. The dry air used in these experiments had a dew point of approximately −35° C. In all cases, the effluent stream then passed through a continuously operating HP5890 Series II Gas Chromatograph equipped with a flame photometric detector (FPD). All of the data were plotted on a normalized time scale of minutes per gram of adsorbent. Details of the experimental conditions are shown in Table 1.

TABLE 1

Sulfur Dioxide Breakthrough Conditions

| Breakthrough Parameter | Value |
|---|---|
| Challenge Concentration | 1000 mg/m$^3$ |
| Temperature | 20° C. |
| RH | 0 |
| Bed height | 4 mm |
| Bed volume | 50 mm$^3$ |
| Flow rate | 20 mL/min at 20° C. |
| Residence time | 0.15 s |
| Detector | GC/FPD |

Figure 14:
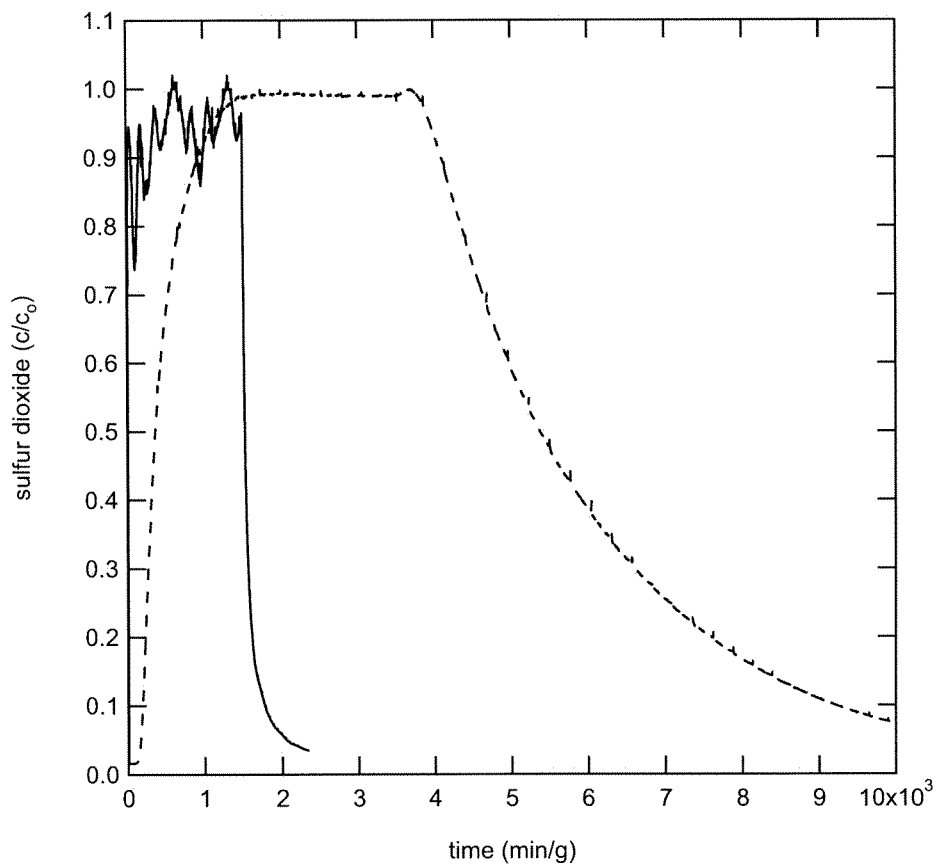
FIG. 14 illustrates adsorption breakthrough curves for sulfur dioxide on glass beads and BPL® activated carbon according to a specific example embodiment of the disclosure.

The consistency of this approach has been documented previously. Breakthrough tests were also performed on all the breakthrough systems using 20×40 mesh glass beads to ensure that the adsorption bed and system were not influencing the breakthrough behavior. No significant time delay was observed for the glass bead runs, nor was any adsorption observed as shown in FIG. 14.

Example 3

Adsorption Isotherms

Nitrogen adsorption isotherms at 77 K were measured using a Quantachrome Autosorb 1A sorption analyzer. The MNPs were out-gassed at 120° C. overnight under vacuum prior to analysis.

Example 4

Fourier Transform Infrared Spectroscopy

A Thermo Fisher 6700 FTIR Spectrophotometer, outfitted with a MCT/A detector and a Golden Gate Mk II ATR top plate outfitted with 2 mm×2 mm diamond crystal ATR (Specac Ltd) and KRS-5 lenses, was used. Background spectra were typically collected at 2 cm$^1$ resolution (128 scans) while samples were collected at 32 scans. Baselines were typically 0.001 AU full scale and spectra were collected in the log (1/R)-wavenumber (cm$^{-1}$) format to facilitate comparison with transmission spectra when available.

Example 5

X-Ray Photoelectron Spectroscopy

XPS spectra were recorded using a Perkin-Elmer Model Phi 570 SAM/ESCA instrument. The binding energy of all peaks was referenced to the carbon s photoelectron peak at 284.6 eV.

Example 6

Magnetic Measurements

Magnetic properties of $CoFe_2O_4$ spinel ferrite nanoparticles were studied using a Quantum Design MPMS-5S SQUID magnetometer with a magnetic field up to 5 T.

Example 7

X-Ray Diffraction

X-ray diffraction was performed with a Panalytical X'pert MPD Powder diffractometer using Cu K-alpha radiation. Variable length divergence and receiving slits were used to keep the illuminated sample area constant. Data were collected over 15-85 degrees at a rate of 0.65 degrees/min.

Example 8

Transmission Electron Microscopy

Transmission electron microscopy studies were performed using a JEOL 100CX2 instrument operating at 100 kV.

Example 9

Elemental Analysis

Elemental analysis was performed using an inductively coupled plasma optical emission spectrometer (IPC), Perkin Elmer OPTIMA 7300DV.

Example 10

Results and Discussion

Figure 15:
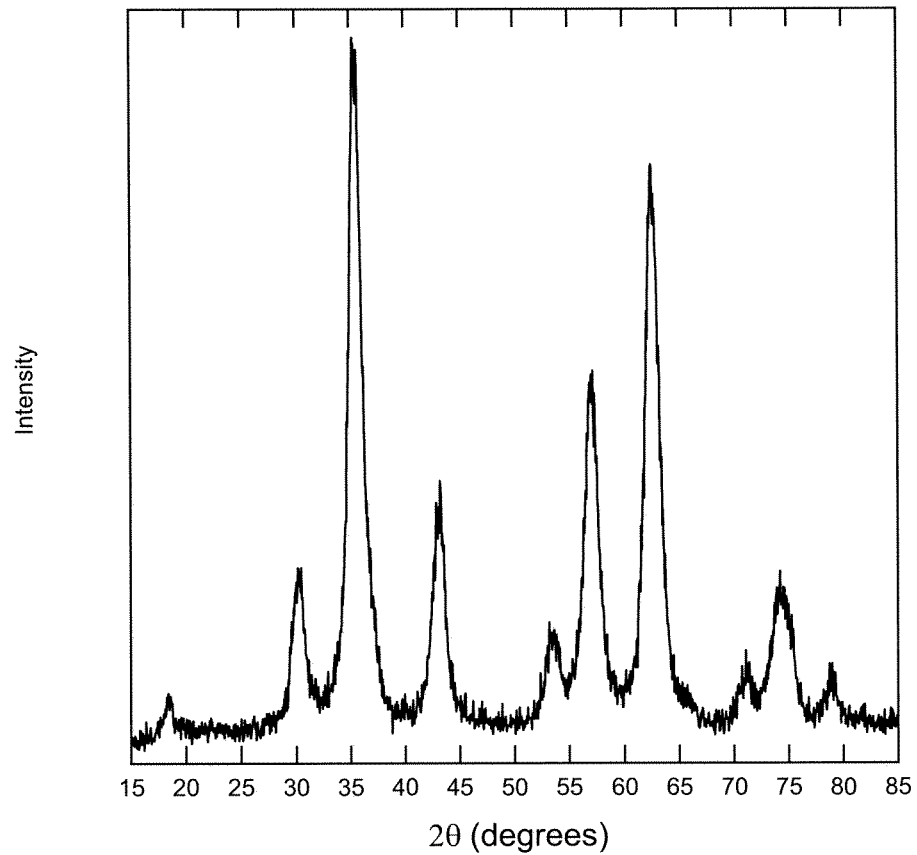
FIG. 15 illustrates an X-ray diffraction pattern showing a well defined $CoFe_2O_4$ spinel crystal according to a specific example embodiment of the disclosure.
Figure 16A:
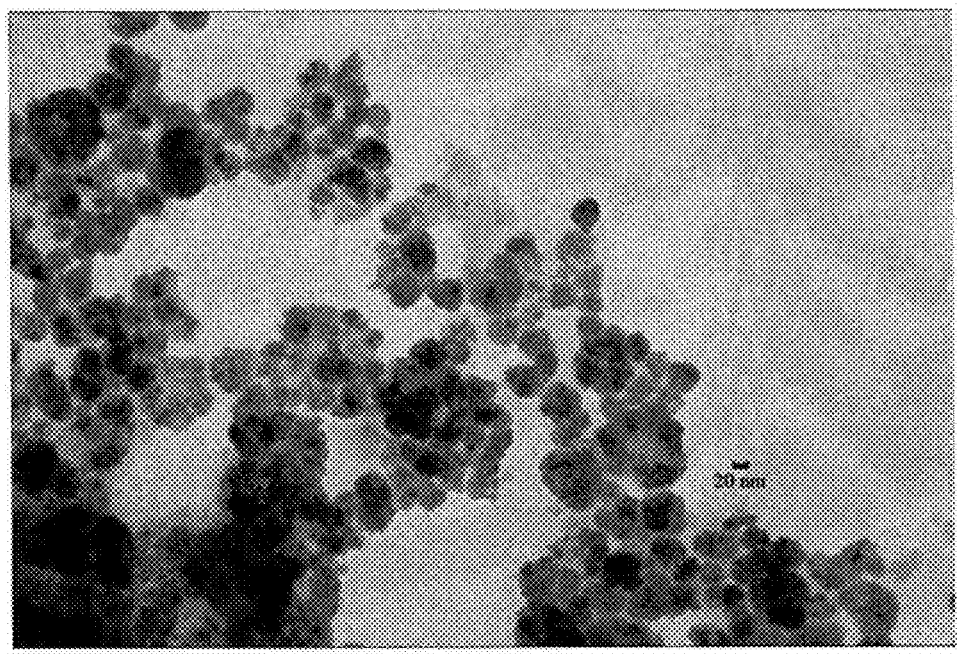
FIG. 16A is a TEM image of $CoFe_2O_4$ MNPs with particle diameters near 20-25 nm according to a specific example embodiment of the disclosure.
Figure 16B:
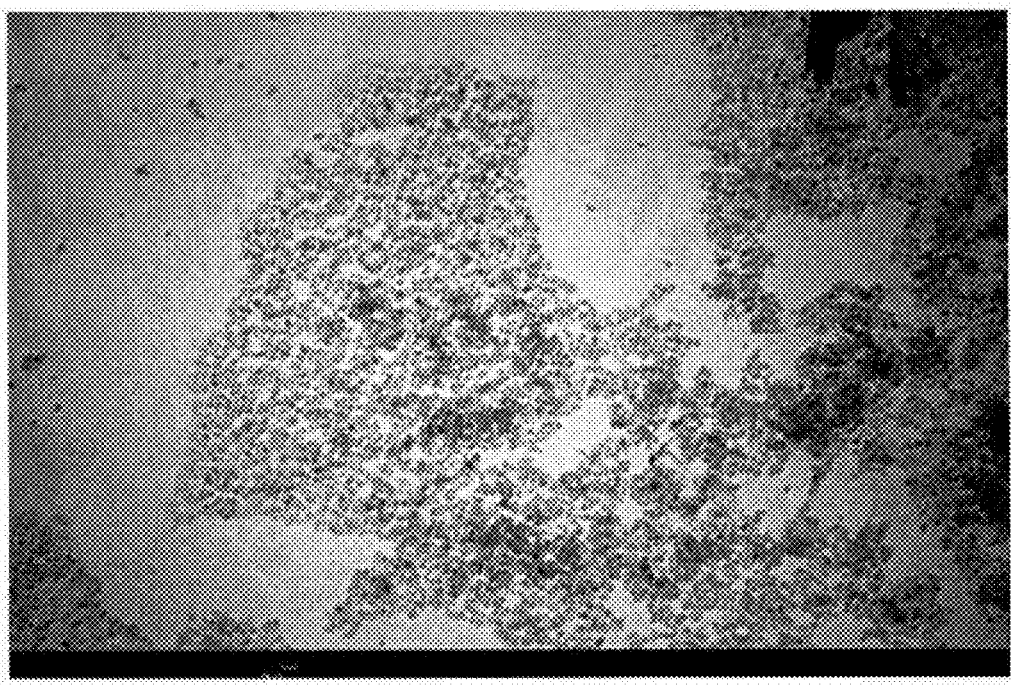
FIG. 16B is a TEM image of $CoFe_2O_4$ MNPs with particle diameters near 4-5 nm according to a specific example embodiment of the disclosure.

As shown in FIG. 15, the XRD pattern of the MNPs is consistent with the spinel structure as reported by others. The Scherer equation was used to estimate a 7.6 nm particle diameter. Transmission electron microscopy (TEM) data on these particlesis shown in FIG. 16B. FIG. 16A is a transmission electron micrograph of a separate batch of MNPs with an approximate size of 20 nm. Inductively Coupled Plasma Atomic Emissions Spectroscopy (ICP-AES) analysis reported a molar ratio of Co to Fe of 1.94, which is consistent with the expected composition of the particles. All of these results provide a high degree of confidence in the quality in both the crystal structure and chemical composition of the MNPs.

Figure 17:
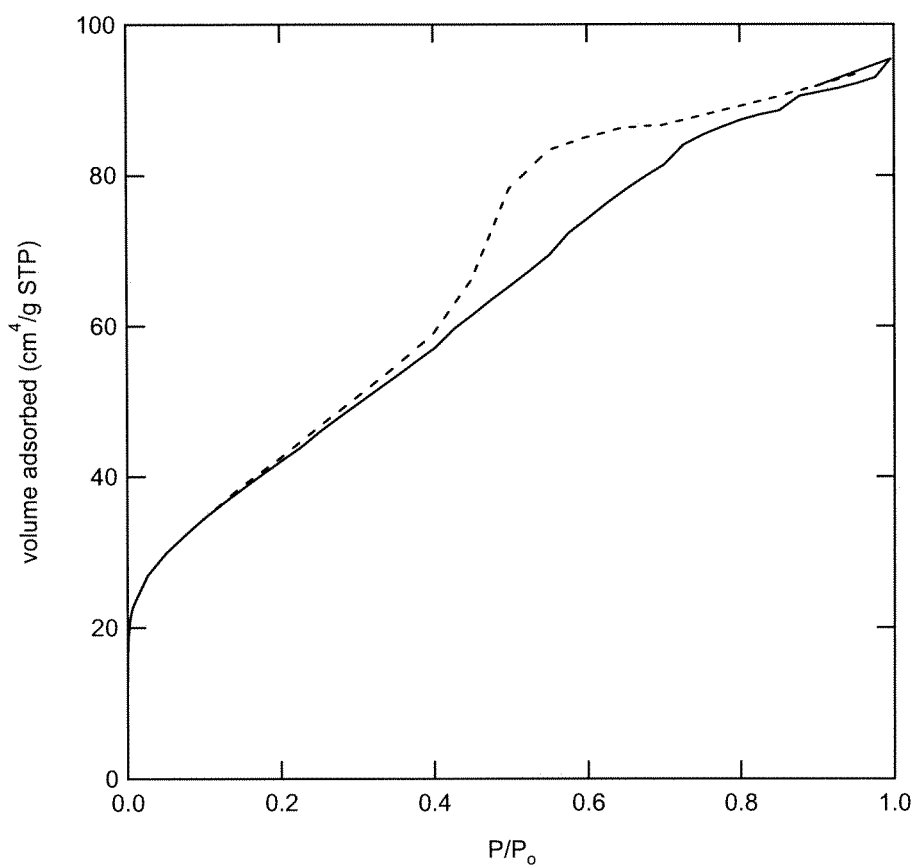
FIG. 17 illustrates nitrogen adsorption isotherms for MNPs according to a specific example embodiment of the disclosure, which provided a BET surface area of 150 $m^2/g$.

Given the nanoscale of these particles some surface area is expected; therefore, nitrogen adsorption isotherms were gathered, as shown in FIG. 17. The adsorption data shows limited nitrogen up take and surface area, as expected of a non-porous particle, with a BET calculated surface area of 150 m$^2$/g.

Figure 18:
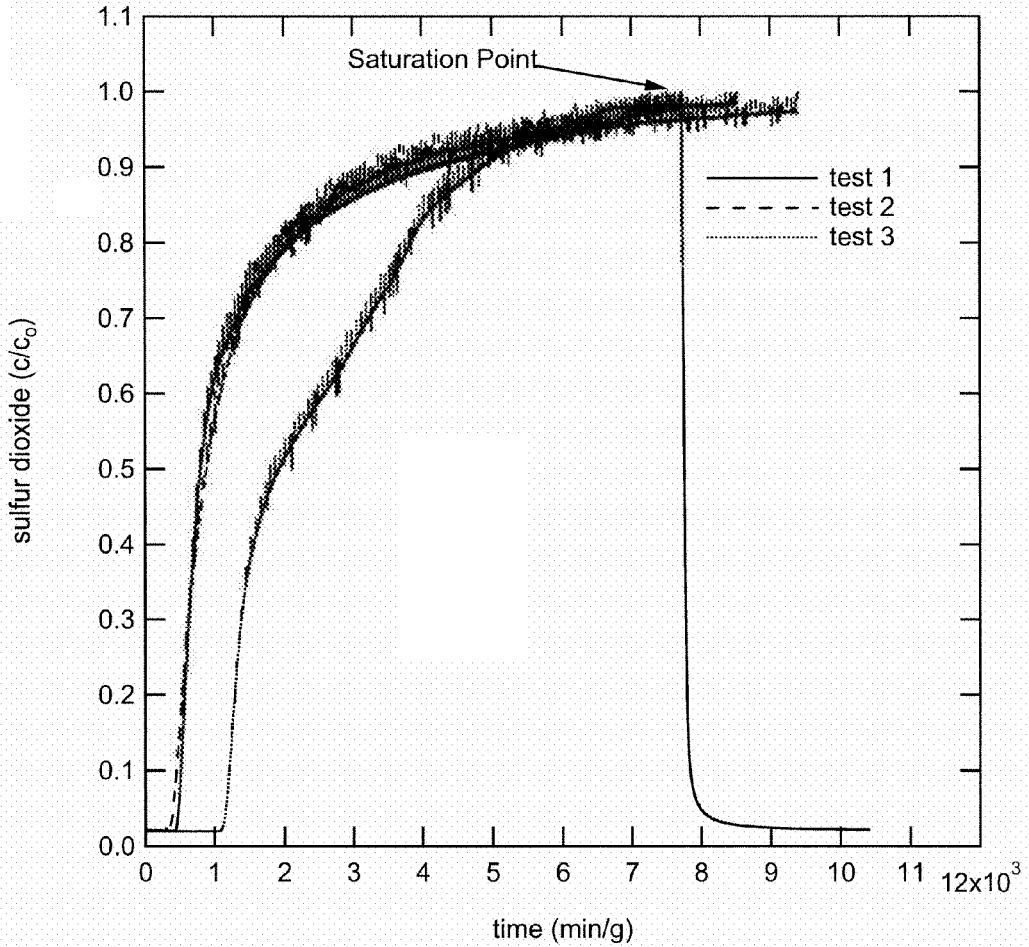
FIG. 18 illustrates adsorption breakthrough curves for sulfur dioxide on MNPs according to a specific example embodiment of the disclosure.

Once characterized the MNPs were subjected to sulfur dioxide breakthrough testing, the results of which are shown in FIG. 18. In this experiment sulfur dioxide was passed over a packed-bed of MNPs and the effluent of the packed-bed monitored until the feed to the bed and the effluent are equal. The experiment was performed three times for accuracy. As a result of different adsorbent mass being used for each test, the breakthrough data shown in FIG. 18 has been normalized on a min/g basis. The mass of adsorbent used for each test is shown in Table 2 and other conditions of the experiment can be found in Table 1.

TABLE 2

Sulfur Dioxide Loadings on MNPs

|  | Test 1 | Test 2 | Test 3 |
|---|---|---|---|
| Adsorbent Mass (g) | 0.062 | 0.057 | 0.053 |
| Loading (mol/kg) | 0.50 | 0.52 | 0.83 |
| Loading with desorption (mol/kg) | 0.48 | — | — |

The results for Test 1 in FIG. 18 show that 62 mg of MNPs adsorbed 1000 mg/m$^3$ of sulfur dioxide completely for approximately 20 minutes. Then sulfur dioxide breaks through the bed and the concentration moves towards the feed in an adsorption wave front. Once at the feed the bed is considered saturated (FIG. 18, arrow), and the sulfur dioxide in the air stream was turned off to allow clean air to pass to the bed. Passing clean air to the bed permitted an evaluation of the strength of the adsorption by determining if clean air will desorb sulfur dioxide from the adsorption surface. FIG. 18 shows only minimal desorption occurs.

The breakthrough data presented in this figure can also be quantified as a dynamic loading by determining the area under the curve as shown elsewhere. In short, a mass balance can be developed that considers how much sulfur dioxide has been passed to the MNPs, then the quantity of sulfur dioxide that has eluted from the column can be subtracted from the feed to determine the loading on the MNPs. Desorption can also be considered and the amount of sulfur dioxide that desorbed can be calculated and subtracted from the loading on the MNPs. This approach provides a dynamic loading that can be examined with or without the consideration of the desorption phenomena.

Applying this process to the breakthrough data presented in FIG. 18 for Test 1 shows that MNPs have a dynamic loading of 0.50 mols/kg without desorption and 0.48 mols/kg when desorption is considered. The breakthrough curves all have a consistent shape, and breakthrough times, and when quantified the curves in this figure yield an average sulfur dioxide dynamic loading of 0.62 mols/kg with a standard deviation of 0.19 mols/kg. The consistently repeatable results provide significant confidence in the calculated loadings.

To further ensure that the adsorption behavior can be attributed to the MNPs and not a dead time response of the system or adsorption of sulfur dioxide on the breakthrough system surfaces, 20×40 mesh glass beads were loaded into the breakthrough device and the sulfur dioxide adsorption experiment was performed again as shown in FIG. 14. It is clear from the breakthrough curve that no quantifiable amount sulfur dioxide adsorption occurs on the breakthrough apparatus surfaces, the dead time of the system is small, and all adsorption can be attributed to the MNPs.

The loading of sulfur dioxide is appreciable when considered in context of its 150 m$^2$/g surface area. For example, BPL® activated carbon was also examined using the breakthrough device, as shown in FIG. 14, and produced a loading of 0.15 mol/kg with no retention after desorption. BPL® has a surface area of 1000 m$^2$/g, or almost tenfold the surface area of MNPs, underscoring the importance of surface chemistry interactions when adsorbing small molecules, which is an idea consistent with results detailed previously on metal organic framework (MOF) materials.

The adsorption conditions utilized in this work are highly dynamic and no effort was made to optimize conditions to ensure gas adsorption. Specifically, the adsorption conditions utilized in this work are the same adsorption conditions used to evaluate highly porous adsorbent materials as documented previously. The results gathered utilizing these conditions provide good evidence of the use of magnetic spinels as adsorbent materials in industrially relevant adsorption conditions.

Figure 19:
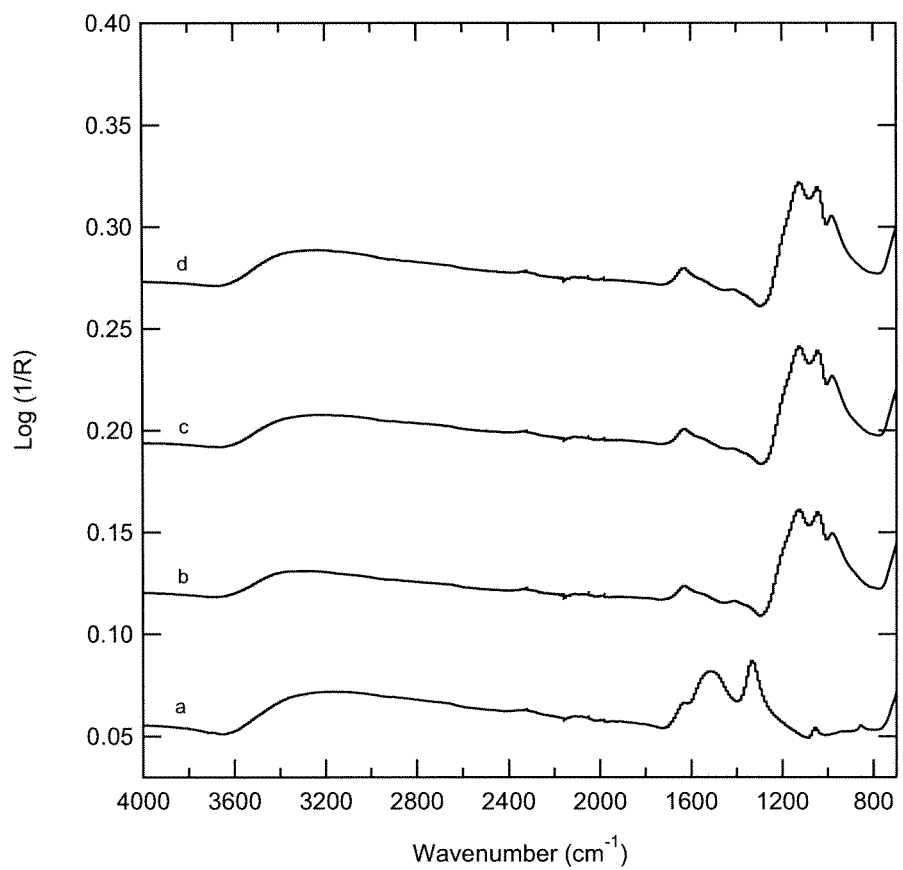
FIG. 19 illustrates FTIR spectra of MNPs according to a specific example embodiment of the disclosure ((a) MNPs before exposure to $SO_2$, (b) MNPs after $SO_2$ exposure Test 1, (c) MNPs after $SO_2$ exposure without desorption Test 2, (d) MNPs after $SO_2$ exposure without desorption Test 3.

To further investigate the surface chemistry of sulfur dioxide adsorption on MNPs, FTIR data was collected on the MNPs after a breakthrough experiment, as shown in FIG. 19. Compared to the unexposed MNP sample, the FTIR data clearly shows adsorbed sulfur species around 1100 cm$^{-1}$, which is consistent with sulfur species as documented by others. For Test 1 the MNPs were subject to desorption; however, for Tests 2 and 3 only adsorption was measured. Regardless of desorption, the FTIR spectra of the samples are nearly identical indicating that sulfur dioxide is retained on the surface of the MNPs. This result is consistent with the breakthrough results, which showed limited desorption.

Figure 20:
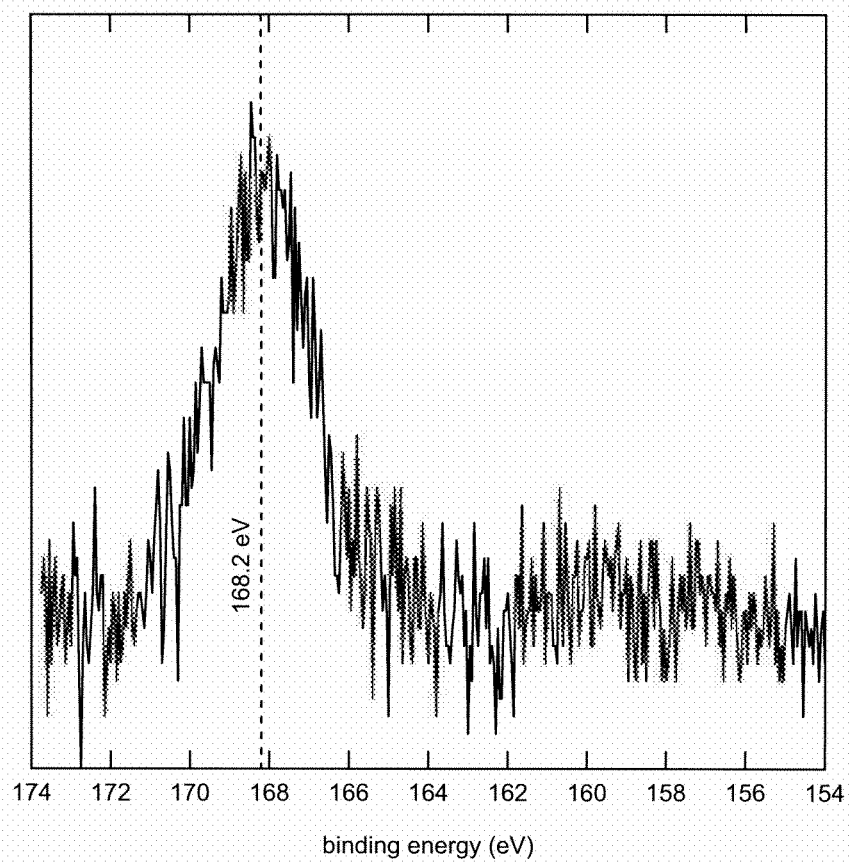
FIG. 20 illustrates XPS spectra of MNPs after sulfur dioxide breakthrough experiment for the sulfur 2p region according to a specific example embodiment of the disclosure.
Figure 21:
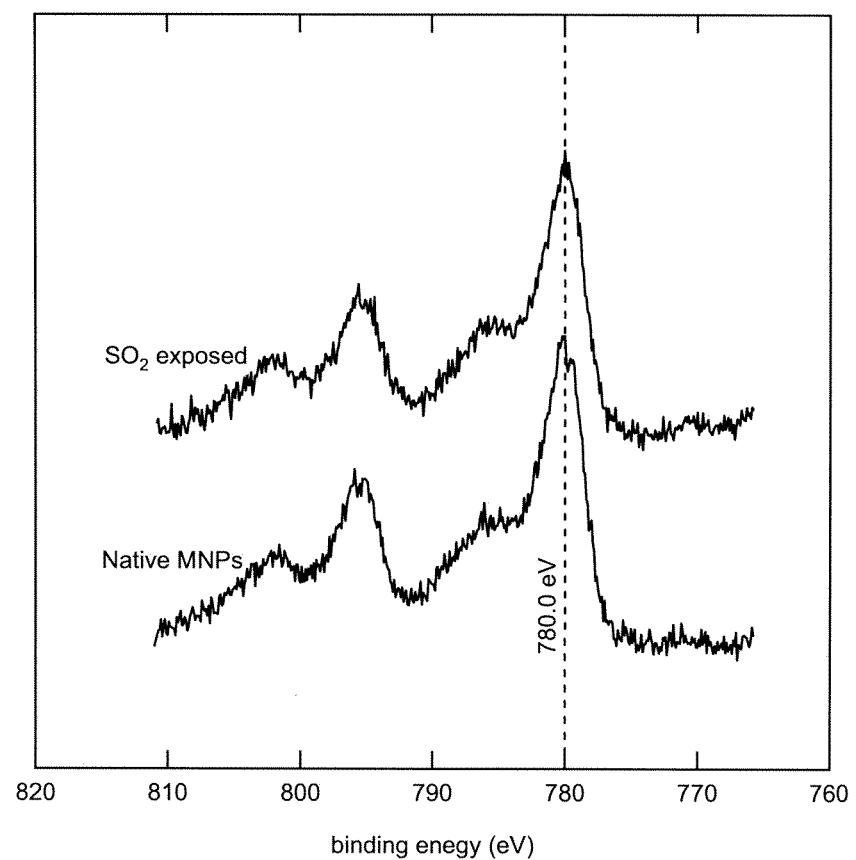
FIG. 21 illustrates XPS spectra of cobalt 2p region according to a specific example embodiment of the disclosure.
Figure 22:
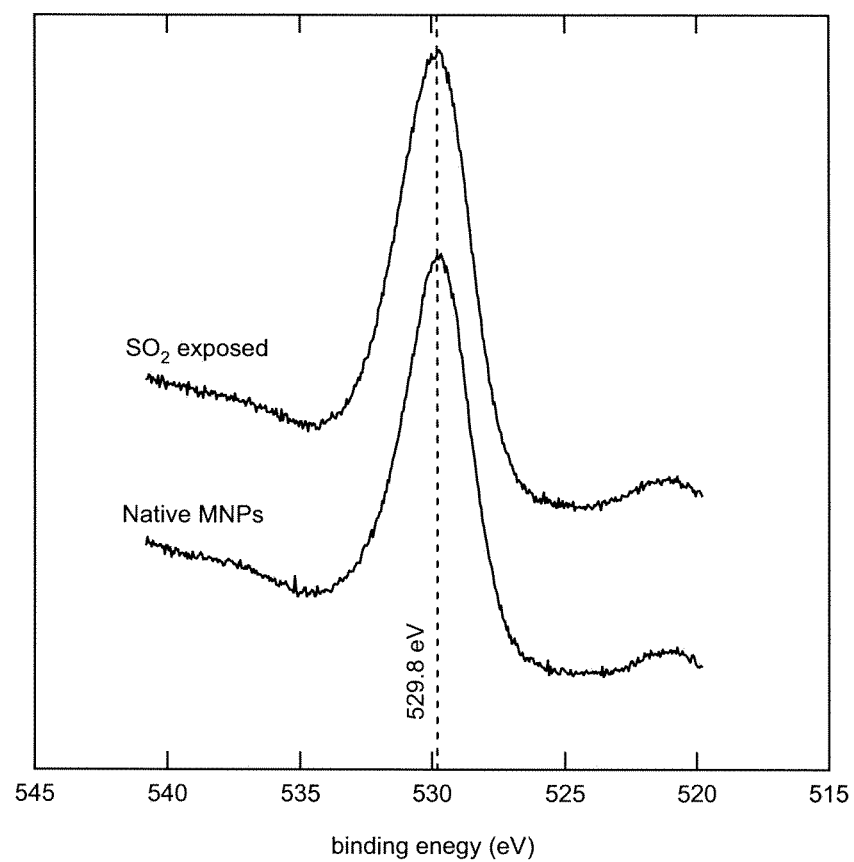
FIG. 22 illustrates XPS spectra of oxygen 1s region according to a specific example embodiment of the disclosure.
Figure 23:
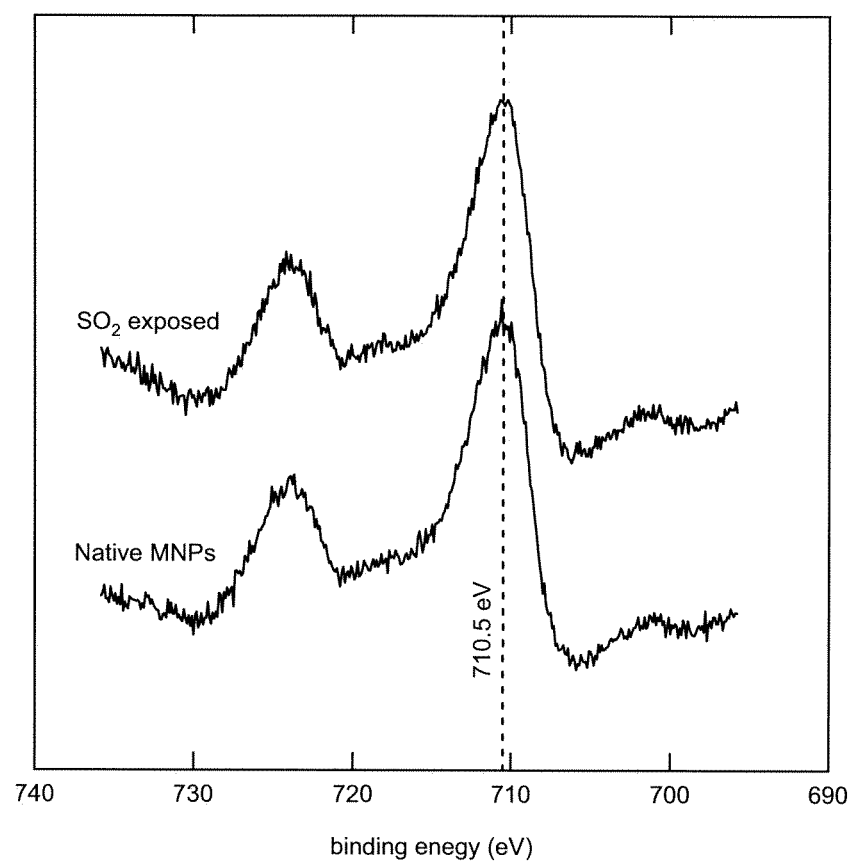
FIG. 23 illustrates XPS spectra of iron 2p according to a specific example embodiment of the disclosure.

Identification of the species of sulfur present by the FTIR data alone is difficult. Therefore, in order to identify more specific information about the type of sulfur species on the surface, XPS data was also gathered on the MNPs both before and after sulfur dioxide adsorption, as shown in FIG. 20. The XPS for the exposed sample has a clear peak at 168 eV that is not seen in the unexposed sample. Additionally, as shown in FIG. 21, FIG. 22, AND FIG. 23, XPS data for cobalt, iron, and oxygen for both the sulfur dioxide exposed and native particles are effectively identical.

Investigation of sulfur dioxide reaction mechanisms on hematite ($\alpha$-Fe$_2$O$_3$) and goethite ($\alpha$-FeOOH) has identified sulfate peaks near 168 eV and sulfite peaks near 167 eV. Therefore, without limiting any particular embodiment to any particular mechanism of action, sulfur dioxide may chemically bind to the surface of CoFe$_2$O$_4$ MNPs as a sulfate. Furthermore, reaction mechanisms with and without the presence of humidity have been considered and a conclusion reached that in the absence of oxygen the following mechanisms may take place:

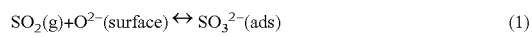

$$SO_2(g) + O^{2-}(\text{surface}) \leftrightarrow SO_3^{2-}(\text{ads}) \quad (1)$$

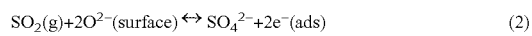

$$SO_2(g) + 2O^{2-}(\text{surface}) \leftrightarrow SO_4^{2-} + 2e^-(\text{ads}) \quad (2)$$

Adsorption of sulfur dioxide is substantially enhanced in the presence of oxygen. Specifically, in the absence of oxygen only a limited amount of sulfate is formed with the sulfite peak dominating the XPS spectra. However, in the presence of oxygen a peak at 168 eV is readily identified as a sulfate. Accordingly, the following mechanisms are proposed in the presence of oxygen:

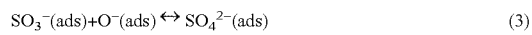

$$SO_3^-(\text{ads}) + O^-(\text{ads}) \leftrightarrow SO_4^{2-}(\text{ads}) \quad (3)$$

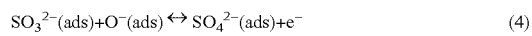

$$SO_3^{2-}(\text{ads}) + O^-(\text{ads}) \leftrightarrow SO_4^{2-}(\text{ads}) + e^- \quad (4)$$

Given the absence of any significant shoulders on the sulfur 2p XPS spectra, as well as the adsorption experiments being conducted in air, it is reasonable that sulfur dioxide adsorption on CoFe$_2$O$_4$ MNPs may result in the formation of a sulfate via mechanisms 2, 3, and/or 4.

Figure 24:
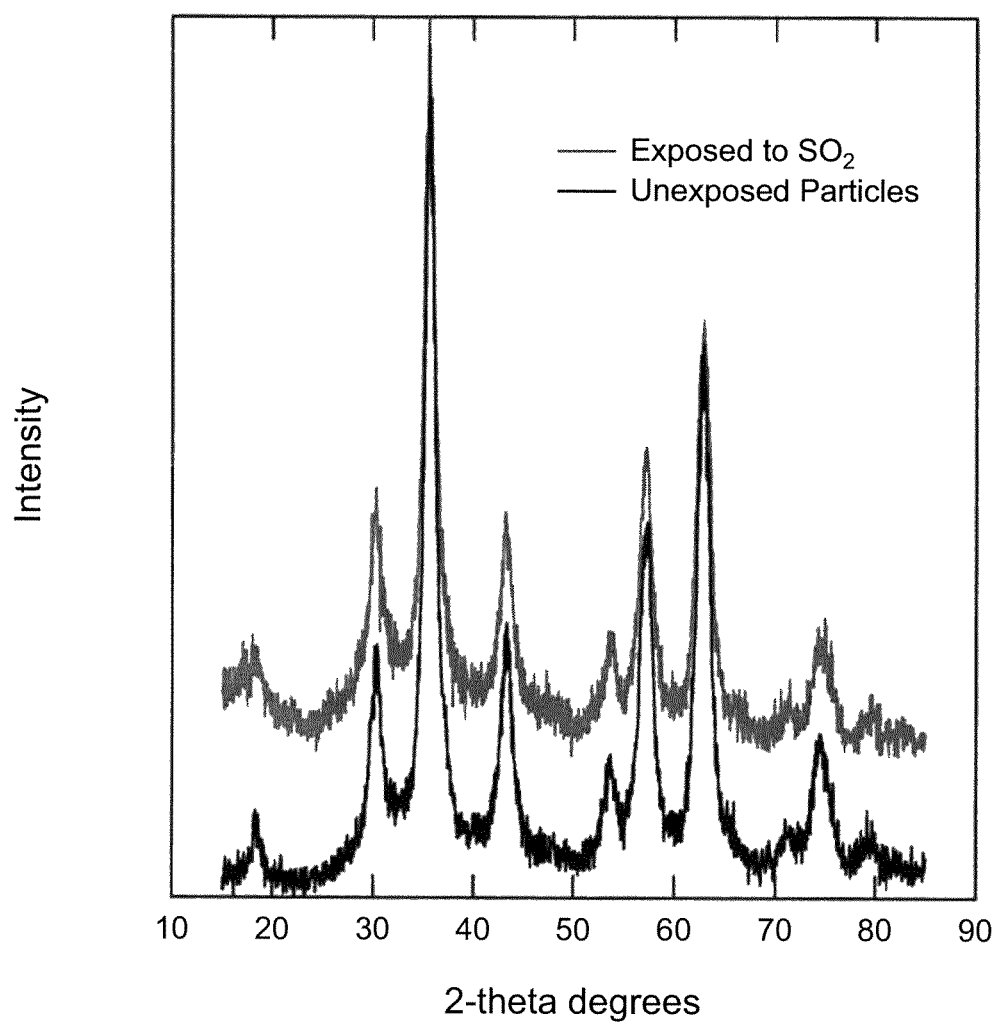
FIG. 24 illustrates XRD data collected from MNPs before (lower trace) and after (upper trace) exposure to silicon dioxide according to a specific example embodiment of the disclosure.

In addition, the XPS spectra of cobalt, iron, and oxygen show that the chemical environment of the majority of the metals atoms in the spinel structure is unchanged with adsorption. This indicates that the adsorption of sulfur dioxide does not destroy the MNP crystal structure. However, to confirm the structural integrity of the particles after sulfur dioxide adsorption XRD data were gathered on the MNPs after exposure. As shown in FIG. 24, the XRD patterns of the MNPs before (lower trace) and after (upper trace) exposure are the same.

Figure 25:
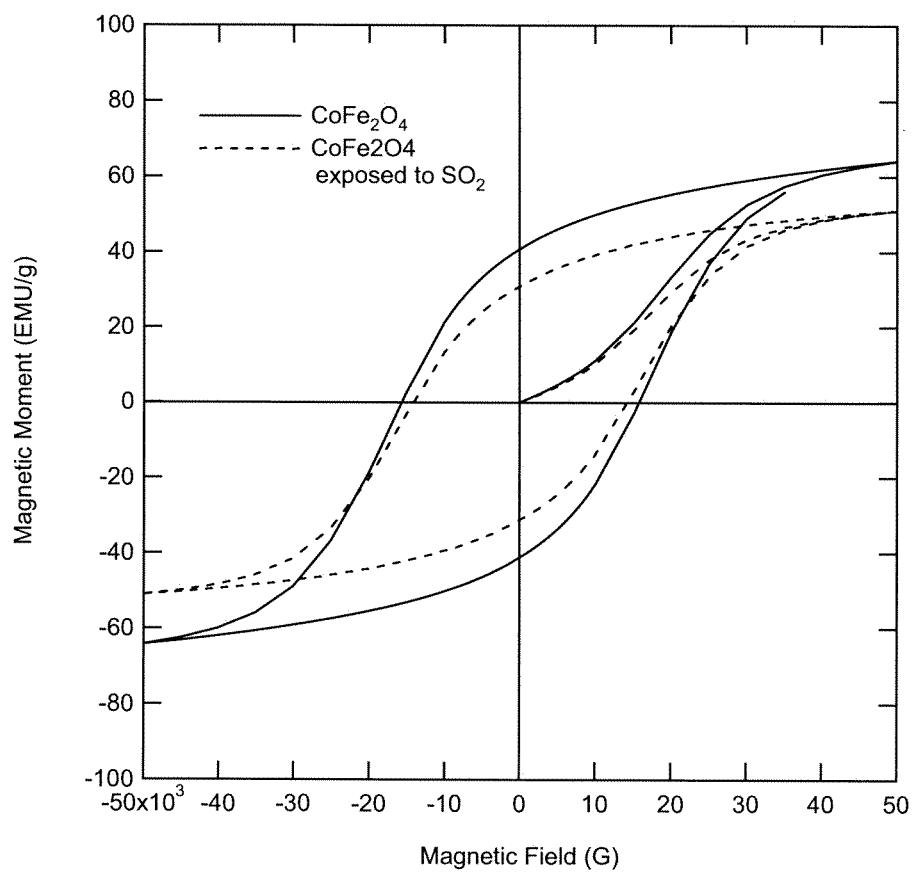
FIG. 25 illustrates magnetic susceptibility curves for MNP both before and after $SO_2$ breakthrough experiments according to a specific example embodiment of the disclosure.

Magnetic measurements of the particles were also taken both before and after sulfur dioxide adsorption experiments as in FIG. 25 and summarized in Table 3. The saturation magnetization, which is near 51 EMU/g for all the tests, is the greatest magnetic moment achieved in the MNPs. The remnant magnetization, which is magnetization of the MNPs that remains after the applied field is removed, is approximately 31 EMU/g after exposure. The magnetic field necessary to return the magnetic moment of the MNPs back to zero after an applied field is, or the coercivity, is approximately 14300 G. These results are interesting when compared to the unexposed MNPs magnetic data, and show the saturation magnetization, remnant magnetization, and coercivity changing by 20%, 23%, and 9% respectively after sulfur dioxide adsorption.

TABLE 3

Magnetization of $CoFe_2O_4$ MNPs before and after sulfur dioxide adsorption

| Sample | Remnant Magnetization EMU/g | % Change | Coercivity G | % Change | Saturation Magnetization EMU/g | % Change |
|---|---|---|---|---|---|---|
| $CoFe_2O_4$ | 40.64 | — | 15714 | — | 64.2 | — |
| $CoFe_2O_4$ after Test 1 | 31.41 | 22.7 | 14430 | 8.2 | 51.40 | 19.9 |
| $CoFe_2O_4$ after Test 2 | 30.79 | 24.2 | 14153 | 9.9 | 51.0 | 20.7 |
| $CoFe_2O_4$ after Test 3 | 31.83 | 21.7 | 14281 | 9.1 | 52.5 | 18.2 |

Without limiting any particular embodiment to any specific mechanism of action, a decrease in coercivity may be attributed to the metal cations at the surface layer of the nanoparticles being coordinated with sulfur dioxide, which reduces the spin-orbital coupling and the surface anisotropy. However, under some circumstances, a reduction in surface anisotropy may explain an increase in saturation magnetization upon loading with benzene ligands. Specifically, the ligands may allow the surface spins to more easily align with the overall magnetization direction and hence increase the saturation magnetization. The influence on surface anisotropy may be a function of the electronic structure of the ligand and its ability to act as a π electron donor. However, in the case of sulfur dioxide loading on $CoFe_2O_4$ MNPs, sulfur dioxide has no π electrons to donate. Therefore, it is reasonable that the formation of a sulfate anion reduces the ability of the electrons to align and reduces the saturation magnetization.

The changes in magnetization are quite significant from an adsorption perspective because they provide a clear indication of an adsorption event. Specifically, the changes in magnetism provide a quantifiable non-destructive means of monitoring adsorption as it occurs on the surface. The results presented here document that adsorption and magnetic changes readily occur on MNPs in gas phase dynamic flow conditions and with small adsorbate molecules. This work also highlights the importance of understanding the surface chemistry of the adsorbent material and that strong adsorption can be readily accomplished in the absence of exceptionally high surface area if the surface chemistry is carefully selected.

The results presented here clearly show that $CoFe_2O_4$ MNPs can function as adsorbent materials for sulfur dioxide. Adsorption loadings of $SO_2$ in dynamic breakthrough conditions were determined to be approximately 0.62 mol/kg, which is significant given the 130 $m^2$/g surface area of the particles. The adsorption proceeds through a chemisorption mechanism with sulfur dioxide forming a sulfate upon adsorption on the particle surface. The crystal structure of the MNP is not destroyed by the adsorption event. In addition, the adsorption event on the surface of the particles decreases the remnant magnetization by approximately 23%, the saturation magnetization by 20%, and the coercivity by approximately 9%. The magnetic changes that occur upon adsorption are significant because quantifiable magnetic changes are rarely seen in adsorbent materials. Furthermore, the use of adsorbent materials that provide an indication of when an adsorption event occurs via magnetism could have broad implications on adsorption based separation. This work provides a key first step to identifying the potential of spinel materials to be used as either adsorbents or indicators.

Example 11

Analysis of Chemical Warfare Agents

A batch of 12 nm $CoFe_2O_4$ nanoparticles was prepared as described previously and characterized with XRD, TEM, ICP-AES to confirm high quality particles had been made. The particles were then divided into 5 portions. One portion was set aside as a control and each of the remaining four portions was exposed to a chemical warfare agent (CWA) stimulant or organophosphate pesticide to verify the assumption that MNPs will exhibit a change in magnetic properties upon exposure to toxic materials. Three toxic chemicals were used in initial testing: dimethyl methylphosphonate (DMMP), the hydrolysis product of Soman pinacolyl methylphosphonate (PMP), and Diazinon. DMMP was also tested on a 50/50 mixture of MNPs and BPL activated carbon. In this experiment a known mass of MNPs was placed in a 20 mL scintillation vial and then liquid CWA simulant was added to the vial. The liquid was always added in excess. The vials were then caped and allowed to sit for approximately 24 hours, after which the caps of the vials were removed and the liquid simulant was allowed to evaporate.

Figure 26:
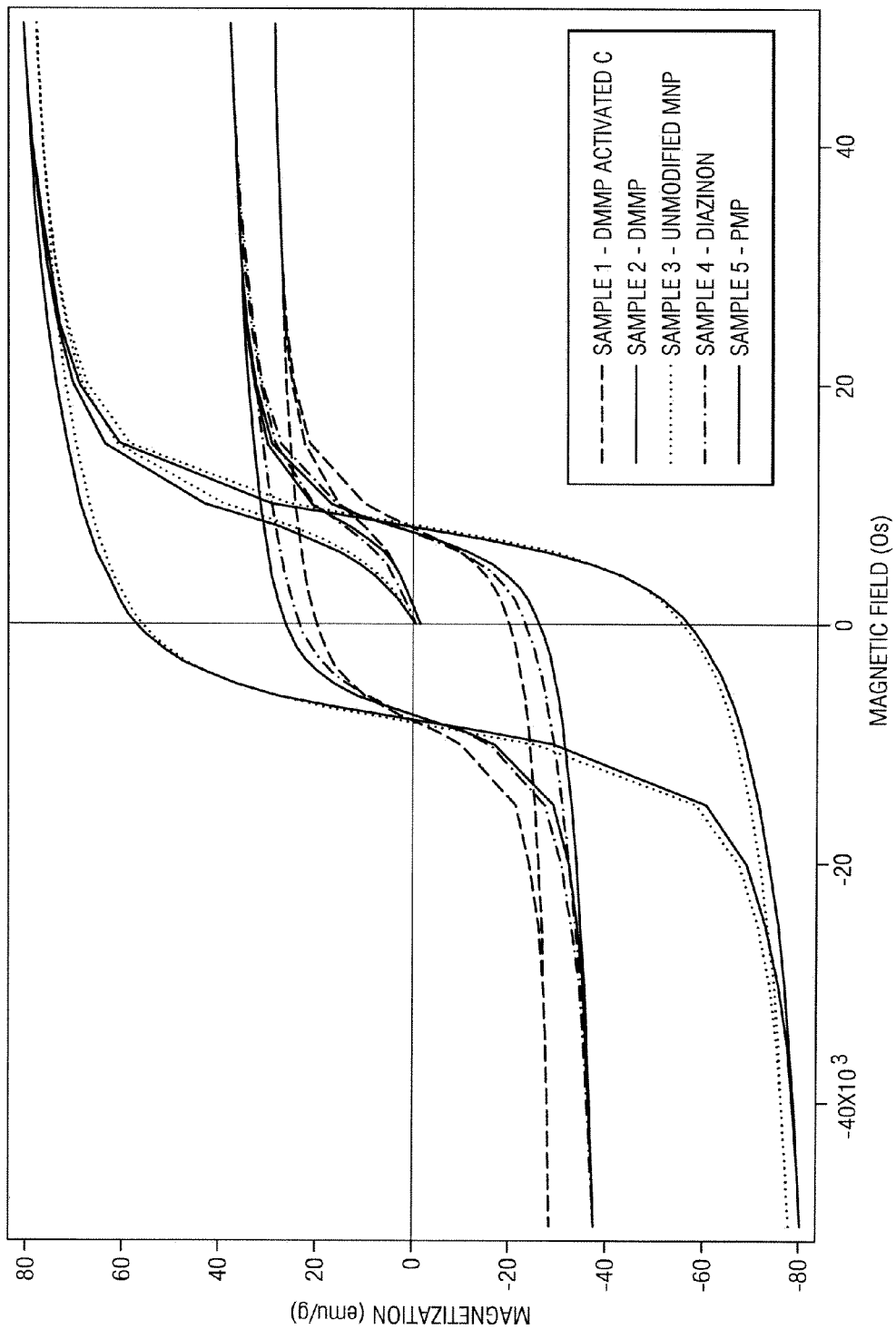
FIG. 26 illustrates MNP saturation magnetization and coercivity changes upon exposure to chemical warfare agent stimulants and organophosphate pesticides according to a specific example embodiment of the disclosure.

Dramatic changes in magnetic properties of these nanoparticles occur when these toxic chemicals are adsorbed as displayed in FIG. 26. The results show the significant changes in the saturation magnetization for the Diazinon and PMP exposed samples. Although limited changes were seen for the DMMP exposed sample, it is possible to envision modifying the surface of the particles to increase the capacity of the materials. Likewise, the changes in magnetism could be altered by changing the crystal phase or chemical composition of the particles.

Since the loading of the toxic materials on the MNPs was not controlled, the magnitude of the resulting changes in magnetic properties cannot be normalized. Therefore, the correlations between the magnetic responses and the particular chemicals/function groups cannot be established at this point. Nevertheless, the results clearly show that the magnetic properties of the exposed nanoparticles are significantly altered from the unexposed MNPs (Table 4). These results provide strong evidence that additional work is needed to examine the potential of this type of technology for monitoring the life-span of adsorbent materials contained in filters.

TABLE 4

Changes in MNP magnetization upon exposure to CWA stimulants.

| Sample | Unmodified MNPs | MNPS DMMP loaded | MNPs mixed with activated carbon and DMMP loaded | MNPs PMP loaded | MNPs Diazinon loaded |
|---|---|---|---|---|---|
| Coercivity (Oe) | 8295 | 8101 | 8089 | 7628 | 7555 |

These results showed that upon exposure to PMP and Diazinon the magnetism of these materials changed by over 50%.

Example 12

Analysis of Ammonia, Chlorine, and Sulfur Dioxide

A batch of 20-25 nm $CoFe_2O_4$ MNPs was prepared as described previously. To determine the potential of MNPs to indicate changes in residual life of filters upon exposure to BFCs and TICs, breakthrough experiments with $SO_2$, $NH_3$, and $Cl_2$ were performed.

Figure 27:
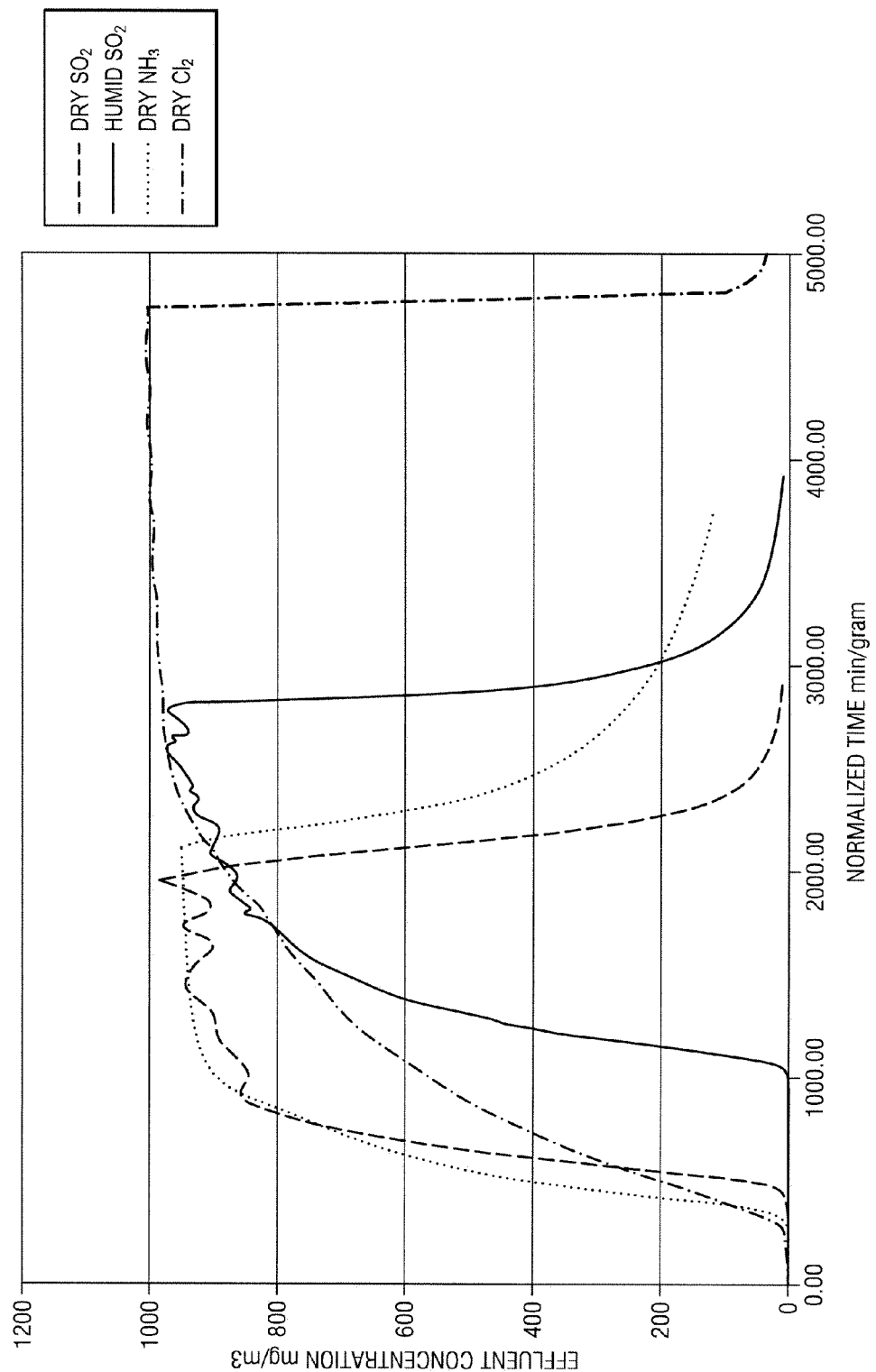
FIG. 27 illustrates breakthrough curves for MNPs according to a specific example embodiment of the disclosure.

The results are intriguing because although MNPs are non-porous, the MNPs are able to adsorb these gases (e.g., in the absence of surface area) as shown by the breakthrough data in FIG. 27. For example, it has been determined from experimental measurements that these materials load 0.25 mol/kg of sulfur dioxide in dry conditions.

In addition, MNPs adsorb 3 mol/kg of ammonia in humid gas streams and 0.7 mols/kg in dry gas streams determined dynamically via breakthrough testing performed similar to testing described elsewhere. In humid conditions on a per mass basis the MNPs adsorb nearly 2 times as much ammonia as traditional carbon. Also, in dry air streams the materials adsorb 20% more ammonia than traditional carbons. However, on a per volume basis MNPs adsorb 4 times the amount of ammonia in humid air and 2 times the amount of ammonia in a dry air stream.

MNPs adsorb chlorine with a loading of 0.3 mol/kg with effectively no desorption of chlorine after the challenge gas is turned off. The loading of chlorine is significant because acid gases can age adsorbent materials and particularly metal impregnated carbons.

These adsorption results are unique because they illustrate increased adsorption capacity with a material that has effectively no surface area relative to traditional materials.

On a per volume basis the MNPs load more $NH_3$ and more $SO_2$ than traditional carbon materials. Thus, a filter filled with MNPs instead of activated carbon might weigh more, but would adsorb twice as much $SO_2$ and $NH_3$. Furthermore, the breakthrough results become more intriguing when they are considered in relation to the magnetic property changes MNPs exhibit when adsorption occurs. Specifically, these results show that MNPs, in addition to showing changes in magnetism when exposed to CWA stimulants, also adsorb appreciable amounts of the battlefield chemical $SO_2$, and the toxic industrial gases $NH_3$ and $Cl_2$. The results clearly document the potential of MNP to indicate the residual life of collective protection filtration system as a result of BFC contamination or CWA events via changes in MNP magnetism.

Example 13

Toxic Chemical-Induced Magnetic Change and Particle Size Correlation

Since the surface to mass ratio changes more drastically in small size nanoparticles, magnetic response studies may be conducted on a series of nanoparticles (e.g., $CoFe_2O_4$ and/or $MnFe_2O_4$) with different mean sizes in the 5-15 nm range for size dependent tests. MNPs of controlled sizes and compositions may be prepared for toxic chemical adsorption and exposure testing. A series of harmful chemicals may be tested. TIC materials may include ammonia, sulfur dioxide, cyanogen chloride, and nitric oxide. Octane and sulfur dioxide may be used as representative BFCs. CWA stimulants may include DMMP, PMP, diazinon, and parathion and the sensitivity of the materials to water may also be determined. Exposure of the MNPs to neat portions of these materials in static conditions may be conducted first. Then additional experiments may examine dosing the MNPs in dynamic conditions, in which the toxic material is blown across the MNPs using a breakthrough device. In the last set of experiments MNPs may be placed on porous substrates, such as activated carbon or MCM-41, and exposed to toxic chemicals in dynamic conditions. Because COOH functional groups are known to bind to the surface of MNPs, adsorbent materials, such as MCM-41 and activated carbon, may be treated to increase the surface concentration of COOH functional groups so as to promote MNP surface coverage on the adsorbent.

Example 14

Magnetic Signal Change and Surface Coverage Correlation

The nature and degree of change in the magnetic response of nanoparticles with surface loading may be assessed conducting experiments to load controlled amounts of toxic materials on the MNPs (e.g., $CoFe_2O_4$ and/or $MnFe_2O_4$). In order to make the MNPs more active towards acid gases, some nanoparticles may be chemically treated so as to enrich the OH ligands on the surface of nanoparticles. The correlation between loading of toxic material on the MNP and changes in magnetic response may allow for the establishment of a working curve for determining the total amount of toxic material in the system in relation to a given magnetic reading. This working curve may be the foundation for the assessment of the remaining life of collective protection filters. DMMP is already known to induce a change in the magnetism of at least some MNPs and it is a common CWA stimulant. For these reasons, it may be the first working curve developed.

What is claimed is:

1. A method for assessing the performance and/or remaining life of an adsorbent material comprising at least one super paramagnetic particle, the method comprising:
    contacting a fluid comprising an adsorbate with the adsorbent material under conditions that permit the adsorbate to contact the at least one super paramagnetic particle, wherein a change in a magnetic property of the at least one super paramagnetic particle occurs upon contact with the adsorbate under the conditions and further wherein the adsorbent material is not subject to stabilization by an external magnetic field;
    detecting the change in the magnetic property of the at least one super paramagnetic particle; and
    comparing the detected change in the magnetic property to a reference to produce an assessment of the performance and/or remaining life of the adsorbent material.

2. A method for assessing the performance and/or remaining life of an adsorbent material according to claim 1, wherein the contacting is continuous, intermittent, periodic, sporadic, haphazard, or combinations thereof.

3. A method for assessing the performance and/or remaining life of an adsorbent material according to claim 1, wherein the detecting is continuous, intermittent, periodic, sporadic, haphazard, or combinations thereof.

4. A method for assessing the performance and/or remaining life of an adsorbent material according to claim 1, wherein the detecting is concurrent with the contacting.

5. A method for assessing the performance and/or remaining life of an adsorbent material according to claim 1, wherein the detecting is non-invasive.

6. A method for assessing the performance and/or remaining life of an adsorbent material according to claim 1, wherein the at least one super paramagnetic particle comprises a crystalline face centered cubic structure.

7. A method for assessing the performance and/or remaining life of an adsorbent material according to claim 1, wherein the at least one super paramagnetic particle comprises a spinel ferrite.

8. A method for assessing the performance and/or remaining life of an adsorbent material according to claim 1, wherein the at least one super paramagnetic particle has the chemical formula $MFe_2O_4$ wherein M represents a transition metal.

9. A method for assessing the performance and/or remaining life of an adsorbent material according to claim 1, wherein the at least one super paramagnetic particle comprises a metal selected from the group consisting of cobalt, copper, iron, magnesium, manganese, nickel, zinc, and/or combinations thereof.

10. A method for assessing the performance and/or remaining life of an adsorbent material according to claim 1, wherein the at least one super paramagnetic particle comprises cobalt, iron, and oxygen.

11. A method for assessing the performance and/or remaining life of an adsorbent material according to claim 1, wherein the at least one super paramagnetic particle has a generally spherical shape or a generally cuboidal shape.

12. A method for assessing the performance and/or remaining life of an adsorbent material according to claim 1, wherein the magnetic property is selected from the group consisting of remnant magnetization, coercivity, saturation magnetization, and combinations thereof.

13. A method for assessing the performance and/or remaining life of an adsorbent material according to claim 1, wherein the adsorbate is selected from the group consisting of Agent 15 (BZ), ammonia, an arsine, arsenic pentafluoride, bis(trifluoromethyl) peroxide, boron tribromide, boron trichloride, boron trifluoride, bromine, bromine chloride, bromomethane, carbon monoxide, chlorine, chlorine pentafluoride, chlorine trifluoride, chloropicrin, cyanogen, cyanogen chloride, cyclosarin (GF), diazinon, diazomethane, diborane, dichloroacetylene, dichlorosilane, dimethyl methylphosphonate (DMMP), disulfur decafluoride, fluorine, formaldehyde (gas), germane, hexaethyl, tetraphosphate, hydrogen azide, hydrogen chloride, hydrogen cyanide, hydrogen selenide, hydrogen sulfide, hydrogen telluride, Lewisite (L), nickel tetracarbonyl, a nitrogen oxide (e.g., nitrogen dioxide), nitrogen mustard (HN-1, HN-2, HN-3), a Novichok agent, oxygen difluoride, pepper spray, perchloryl fluoride perfluoroisobutylene, phosgene, phosgene oxime (CX), phosphine, phosphorus pentafluoride, pinacolyl methylphophonate (PMP), sarin (GB), selenium hexafluoride, silicon tetrachloride, silicon tetrafluoride, soman (GD), stibine, surfur mustard (HD, H), sulfur dioxide, sulfur tetrafluoride, tabun (GA), tear gas, tellurium hexafluoride, tetraethyl dithiopyrophosphate, tetraethyl pyrophosphate, trifluoro acetylchloride, tungsten hexafluoride, VR, VX, and combinations thereo.

14. A method for assessing the performance and/or remaining life of an adsorbent material according to claim 1, wherein the reference comprises at least one magnetic property of the at least one super paramagnetic particle prior to contact with the fluid.

15. A method for assessing the performance and/or remaining life of an adsorbent material according to claim 1, wherein the detecting further comprises detecting the magnetic property of the at least one super paramagnetic particle prior to the contacting to form the reference.

16. A method for assessing the performance and/or remaining life of an adsorbent material according to claim 1, wherein the reference comprises at least one magnetic property of a second at least one super paramagnetic particle, wherein the at least one super paramagnetic particle is identical to the second at least one super paramagnetic particle except the second at least one super paramagnetic particle is naive to the adsorbate.

* * * * *